(12) United States Patent
Nomura et al.

(10) Patent No.: US 7,796,240 B2
(45) Date of Patent: Sep. 14, 2010

(54) EVALUATION METHOD AND MANUFACTURING METHOD OF LIGHT-EMITTING ELEMENT MATERIAL, MANUFACTURING METHOD OF LIGHT-EMITTING ELEMENT, AND LIGHT-EMITTING DEVICE AND ELECTRIC APPLIANCE HAVING LIGHT-EMITTING ELEMENT

(75) Inventors: Ryoji Nomura, Kanagawa (JP); Satoshi Seo, Kanagawa (JP); Kumi Kojima, Tokyo (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 9 days.

(21) Appl. No.: 12/396,663

(22) Filed: Mar. 3, 2009

(65) Prior Publication Data

US 2009/0168048 A1    Jul. 2, 2009

Related U.S. Application Data

(63) Continuation of application No. 11/411,872, filed on Apr. 25, 2006, now Pat. No. 7,505,122.

(30) Foreign Application Priority Data

Apr. 28, 2005    (JP)    ............................. 2005-131565

(51) Int. Cl.
*G01B 11/16*    (2006.01)
*G01N 21/00*    (2006.01)

(52) U.S. Cl. .................. 356/32; 356/432; 356/433; 428/690

(58) Field of Classification Search ............... 356/32, 356/432, 433; 428/690
See application file for complete search history.

(56) References Cited

U.S. PATENT DOCUMENTS 6,816,255 B2    11/2004    Mank et al.
2008/0003455 A1    1/2008    Li et al.

FOREIGN PATENT DOCUMENTS

JP    2004-277377    10/2004

*Primary Examiner*—L. G Lauchman
(74) *Attorney, Agent, or Firm*—Husch Blackwell Sanders LLP

(57) ABSTRACT

The present invention provides an evaluation method for evaluating whether a light-emitting element material to be evaluated is suitable for a host material or a guest material. By carrying out a first step of measuring absorption intensity of a light-emitting element material and a second step of irradiating the light-emitting element material with light for a predetermined period of time, repeatedly; thereby a change in absorption intensity with time is evaluated so that whether the light-emitting material is suitable for a host material or a guest material can be distinguished. The light emitted to the light-emitting element material preferably has a wavelength component which is absorbed by a skeleton which contributes to excitation of the light-emitting element material.

14 Claims, 24 Drawing Sheets

EVALUATION METHOD AND MANUFACTURING METHOD OF LIGHT-EMITTING ELEMENT MATERIAL, MANUFACTURING METHOD OF LIGHT-EMITTING ELEMENT, AND LIGHT-EMITTING DEVICE AND ELECTRIC APPLIANCE HAVING LIGHT-EMITTING ELEMENT

This application is a continuation of application Ser. No. 11/411,872 filed on Apr. 25, 2006 now U.S. Pat. No. 7,505,122.

BACKGROUND OF THE INVENTION

1. Field of the Invention

The present invention relates to an evaluation method of a light-emitting element material. In particular, the present invention relates to an evaluation method for distinguishing a function of a light-emitting element material. In addition, the present invention relates to a light-emitting element having a material to which the evaluation method is applied.

2. Description of the Related Art

In a light-emitting element in which light is emitted by current flowing between electrodes due to hopping of carriers between energy levels, an operation characteristic is greatly affected by an oxidation-reduction potential, electrochemical stability, and the like of a material. Therefore, in the development of a light-emitting element material, an oxidation-reduction potential, electrochemical stability, and the like are examined by cyclic voltammetry measurement and whether the manufactured material is suitable for a light-emitting element material or not is evaluated (For example, Patent Document 1).

However, there is a case where reliability of a light-emitting element, especially reliability of a life-time thereof, is unfavorable even when the element is manufactured by using a material which is distinguished to be suitable based on the data of an oxidation-reduction potential, electrochemical stability, and the like.

[Patent Document 1]

Japanese Patent Application Laid-Open No. 2004-277377 (Embodiment 2)

SUMMARY OF THE INVENTION

One of the objects of the present invention is to provide an evaluation method of a light-emitting element material in which a material is evaluated for suitability as a host material or a guest material. In addition, it is another object of the present invention to provide a manufacturing method of a light-emitting element material in which deterioration in luminance associated with accumulation of light-emitting time is small.

Inventors of the present invention have found that there is a correlation between a life-time of a light-emitting element and photochemical stability of a light-emitting element material used as a host material or a guest material of the light-emitting element. Moreover, the inventors have found that by examining photochemical stability of a manufactured light-emitting element material, the suitability of the light-emitting element material as a host material or a guest material can be evaluated. Here, photochemical stability of a light-emitting element material may be examined by a step of applying stress to the light-emitting element material for a predetermined period of time and a step of measuring absorption intensity, which are conducted repeatedly to measure a change in absorption intensity with time associated with accumulation of stress. Light having a wavelength component which is absorbed by a skeleton that contributes to excitation of the light-emitting element material is preferably used as the stress applied to the light-emitting element material.

In this specification, a light-emitting element has at least a light-emitting layer between a pair of electrodes. A light-emitting element material is a material used for forming a light-emitting element and which is contained in a light-emitting layer. An evaluation method of a light-emitting element material according to the present invention comprises a first step of measuring absorption intensity of the light-emitting element material and a second step of irradiating the light-emitting element material with light for a predetermined period of time, which are carried out repeatedly; thereby a change in absorption intensity associated with accumulation of light-irradiation time is evaluated. Here, the light applied in the second step preferably has a wavelength component which is absorbed by a skeleton that contributes to excitation of the light-emitting element material.

A manufacturing method of a light-emitting element material according to the present invention comprises a process of evaluating the light-emitting element material in which a first step of measuring absorption intensity of the light-emitting element material and a second step of irradiating the light-emitting element material with light for a predetermined period of time are carried out repeatedly, and a change in absorption intensity associated with accumulation of light-irradiation time is evaluated. Here, the light applied in the second step preferably has a wavelength component which is absorbed by a skeleton that contributes to excitation of the light-emitting element material.

A light-emitting element material according to the present invention which is manufactured by a manufacturing method of the light-emitting element material comprises a process of evaluating the light-emitting element material in which a first step of measuring absorption intensity of the light-emitting element material and a second step of irradiating the light-emitting element material with light for a predetermined period of time are carried out repeatedly, and a change in absorption intensity associated with accumulation of light-irradiation time is evaluated. Here, the light applied in the second step preferably has a wavelength component which is absorbed by a skeleton that contributes to excitation of the light-emitting element material.

A light-emitting device according to the present invention has a light-emitting layer between a pair of electrodes. The light-emitting layer contains a light-emitting element material which is manufactured by a manufacturing method comprising a process of evaluating the light-emitting element material in which a first step of measuring absorption intensity of the light-emitting element material and a second step of irradiating the light-emitting element material with light for a predetermined period of time are carried out repeatedly, and a change in absorption intensity associated with accumulation of light-irradiation time is evaluated. Here, the light applied in the second step preferably has a wavelength component which is absorbed by a skeleton that contributes to excitation of the light-emitting element material.

A light-emitting device according to the present invention has a light-emitting layer between a pair of electrodes. The light-emitting layer contains a light-emitting element material which is evaluated by an evaluation method comprising repeatedly carrying out a first step of measuring absorption intensity of the light-emitting element material and a second step of irradiating the light-emitting element material with light for a predetermined period of time, and a change in absorption intensity associated with accumulation of light-irradiation time is evaluated. The light-emitting element material is used for manufacturing the light-emitting element, in which a decreasing ratio of the absorption intensity after the light irradiation is 20% or less when the sum of light-irradiation time is 100 minutes. Here, the light irradiated in the second step preferably has a wavelength component which is absorbed by a skeleton that contributes to excitation of the light-emitting element material. The decreasing ratio of the absorption intensity is a decreasing ratio to the absorption intensity of the initial state.

A light-emitting device of the present invention has a light-emitting layer between a pair of electrodes. The light emitting layer contains an anthracene derivative in which a decreasing ratio of absorption intensity is 20% or less after the light irradiation for 100 minutes with light having a wavelength component of 320 nm or more. The decreasing ratio of the absorption intensity is a decreasing ratio to the absorption intensity of the initial state.

According to the present invention, whether a light-emitting element material is suitable for a host material or a guest material can be evaluated without manufacturing a light-emitting element using the light-emitting element material. Accordingly, a light-emitting element material suitable for being used as a host material or a guest material can be manufactured at low cost.

DETAILED DESCRIPTION OF THE INVENTION

Embodiment Mode 1

An example of an evaluation method for a light-emitting element material according to the present invention is described.

Figure 2A:
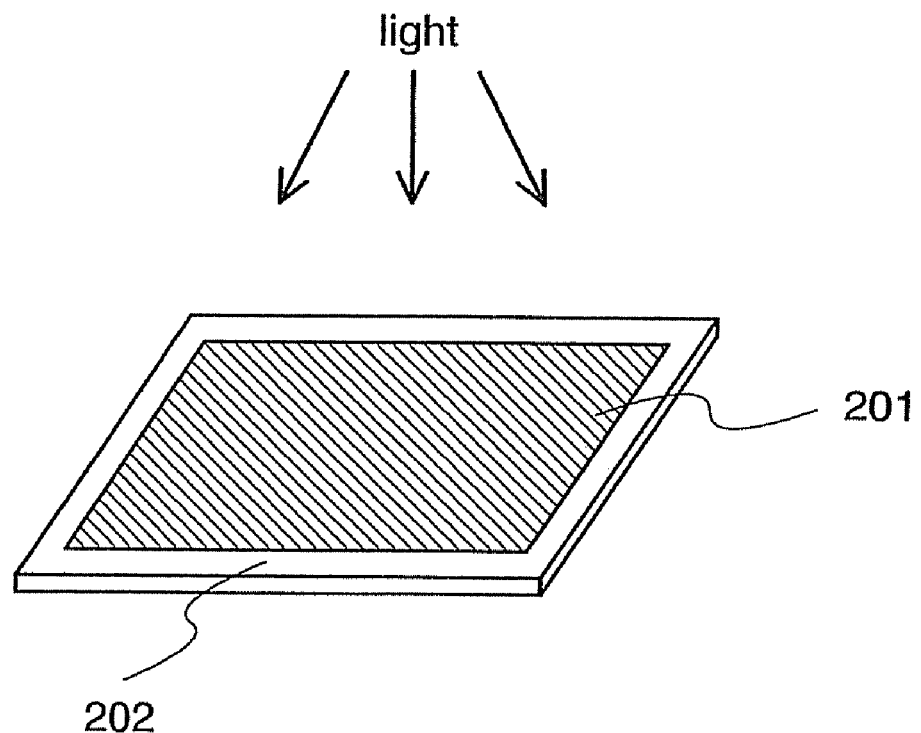
FIGS. 2A and 2B show an evaluation method of a light-emitting element material according to the present invention.
Figure 2B:
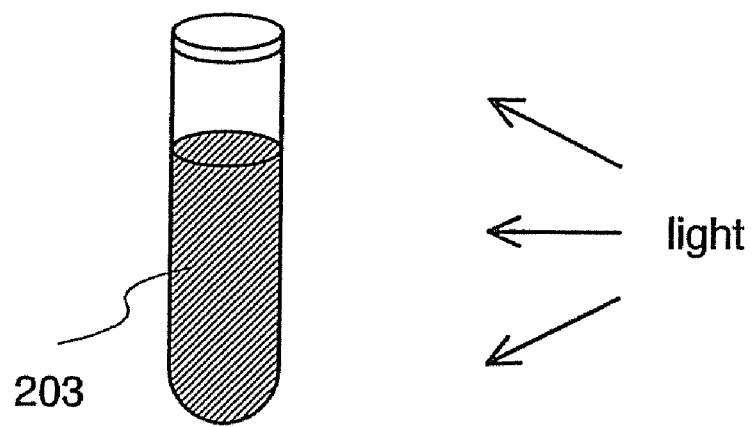

For the evaluation, a substrate 201 with a film 202 formed from a light-emitting element material shown in FIGS. 2A and 2B may be used. For the substrate 201, a material such as quartz or glass which transmits light with a wavelength of 300 nm or more, may be used. In addition, a solution 203 in which a light-emitting element material is dissolved may be used as a sample. In this case, methylene chloride, chloroform, or the like is preferably used as a solvent for dissolving the light-emitting element material.

Figure 1:
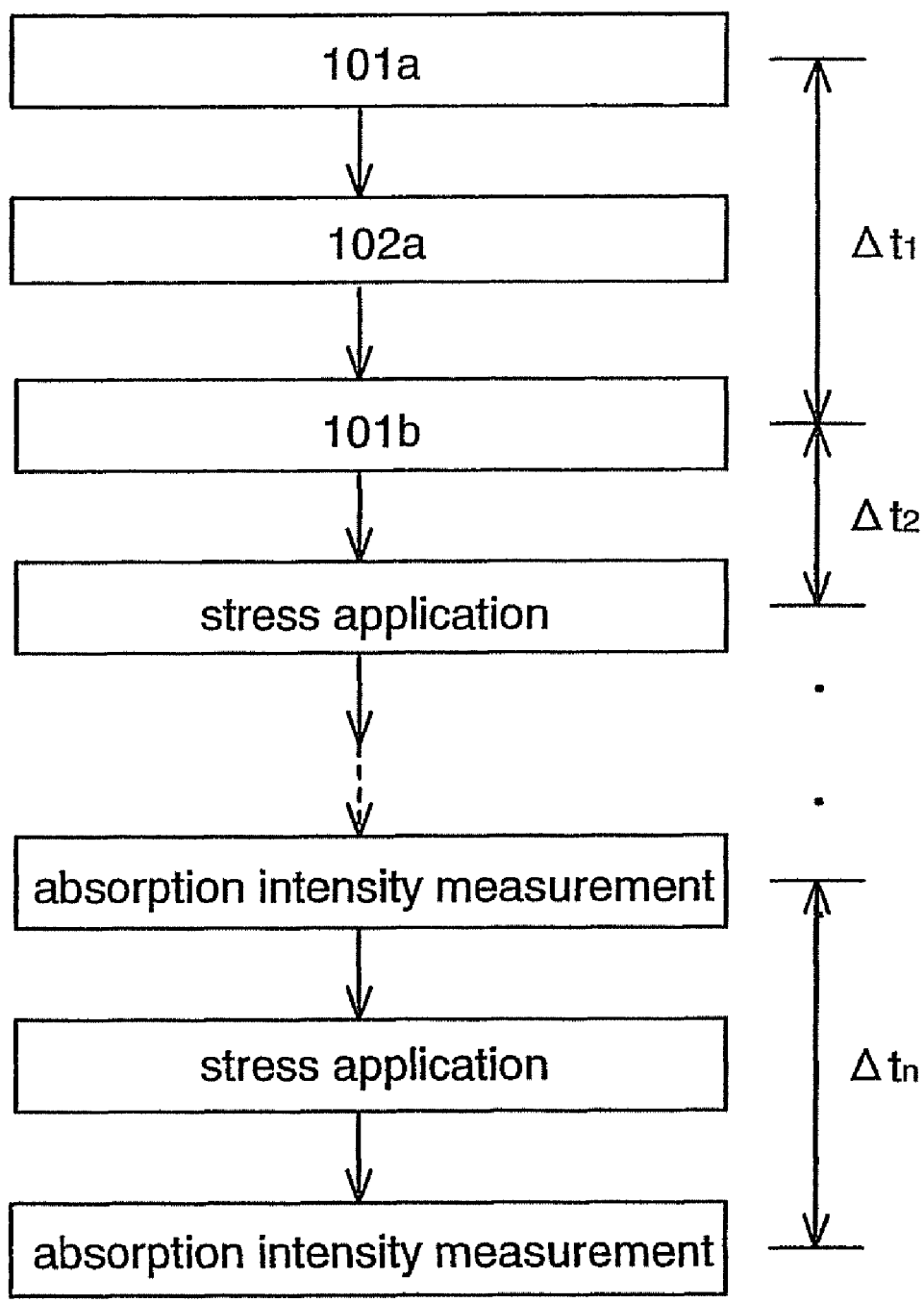
FIG. 1 shows an evaluation method of a light-emitting element material according to the present invention.

A measurement method of photochemical stability is described with reference to FIG. 1. First, the sample is irradiated with light and an absorption spectrum is measured to measure absorption intensity for an arbitrary wavelength in an ultraviolet region in an initial state (an absorption intensity measurement 101a). Then, the sample is irradiated with light, from which light with a short wavelength of 300 nm or less (preferably, 320 nm or less) is removed for a determined period of time ($\Delta t_1$) (stress application 102a), and then, an absorption intensity measurement 101b is carried out. As described above, an absorption intensity measurement and stress application are repeatedly carried out. Absorption intensity is plotted against the sum of time in which stress is applied ($\Delta t_1 + \Delta t_2 + \ldots + \Delta t_n + \ldots$) and a change in absorption intensity associated with accumulation of stress applied by light irradiation is examined. Note that a period of time for applying stress (including both time of application in one step and the sum of time) is not particularly limited.

Here, light applied as stress is preferably light from which light with a short wavelength is removed and has a wavelength component which is absorbed by a skeleton that particularly contributes to excitation in a compound used as a light-emitting element material. For example, when the light-emitting element material is an anthracene derivative and the light-emitting element material is excited by an anthracene skeleton, light having a wavelength region of 320 to 420 nm which is absorbed by the anthracene skeleton is preferably applied as stress.

According to the result of the measurement of photochemical stability described above, it is suggested that a light-emitting element material has photochemical stability when a change in absorption intensity associated with an increase in the sum of time in which stress is applied is small. That is, the light-emitting element material has resistance to repetition of alternately being in an excited state and being in a ground state and is suitable for a host material or a guest material. On the other hand, when a large change in absorption intensity associated with an increase in the sum of time in which stress is applied is observed, the material is photochemically unstable and is unsuitable for a host material or a guest material.

As described above, by evaluating photochemical stability of a light-emitting element material, the stability of the light-emitting element material as a host material or a guest material can be examined. That is, whether a light-emitting element material is suitable for a host material or a guest material can be determined without manufacturing a light-emitting element with the light-emitting element material and evaluating a deterioration characteristic of the light-emitting element.

Embodiment Mode 2

In this embodiment mode, an example of a light-emitting element which is manufactured using a light-emitting element material defined to be suitable for a host material or a guest material by the evaluation method in Embodiment Mode 1 is described with reference to FIG. 3.

Figure 3:
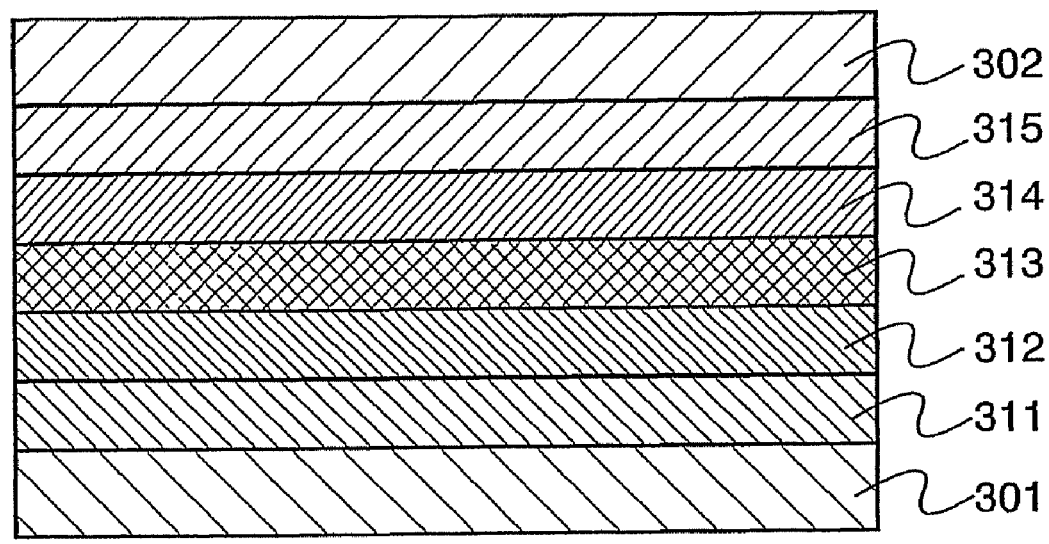
FIG. 3 shows a light-emitting element manufactured using a guest material or a host material manufactured with an evaluation method of a light-emitting element material according to the present invention.

FIG. 3 shows a light-emitting element which has a light-emitting layer 313 between a first electrode 301 and a second electrode 302. The light-emitting layer 313 contains a light-emitting element material which is manufactured through a process of evaluating photochemical stability by an evaluation method of a light-emitting element material according to the present invention.

In such a light-emitting element, holes injected from the first electrode 301 and electrons injected from the second electrode 302 are recombined in the light-emitting layer 313. Then, a guest is excited. The guest of the present invention in the excited state emits light when returning to a ground state. Note that the guest can be brought to the excited state directly by recombination of carriers, or indirectly by energy transferred to the guest from the host, which is brought to the excited state by recombination of carriers.

Here, a host is a main component contained in the light-emitting layer 313 and has an energy gap larger than that of the guest. The guest is contained in the light-emitting layer 313 dispersedly in the layer formed from the host. The guest is a compound which emits light preferentially when the light-emitting element is driven. Note that the energy gap is an energy gap between a LUMO level and a HOMO level. Such a light-emitting layer containing a host and a guest can be formed by evaporating materials in a plurality of evaporation sources provided in one treatment chamber concurrently. The material used for forming a light-emitting layer is called a guest material or a host material depending on its function in the light-emitting element.

The first electrode 301 and the second electrode 302 are not particularly limited. They can be formed by using gold (Au), platinum (Pt), nickel (Ni), tungsten (W), chromium (Cr), molybdenum (Mo), iron (Fe), cobalt (Co), copper (Cu), palladium (Pd), or the like, in addition to indium tin oxide (ITO), indium tin oxide containing silicon oxide, or indium oxide containing 2 to 20% of zinc oxide. The first electrode 301 can also be formed using an alloy of magnesium and silver, an alloy of aluminum and lithium, or the like, in addition to aluminum. Note that, a method for forming the first electrode 301 and the second electrode 302 is not particularly limited and a sputtering method, an evaporation method, or the like may be used. To take out emitted light to the outside, one or both of the first electrode 301 and the second electrode 302 is/are preferably formed by using indium tin oxide or the like. Alternatively, one or both of the first electrode 301 and 302 is/are preferably formed by using silver, aluminum, or the like to have a thickness of several nm to several tens nm so that visible light can pass therethrough.

As shown in FIG. 3, a hole-transporting layer 312 may be provided between the first electrode 301 and the light-emitting layer 313. The hole-transporting layer is a layer having a function of transporting holes injected from the first electrode 301 side to the light-emitting layer 313. Providing the hole-transporting layer 312 makes it possible to isolate the first electrode 301 from the light-emitting layer 313. Consequently, it is possible to prevent light emission from going out due to a metal contained in the first electrode 301. The hole-transporting layer is preferably formed using a substance having a high hole-transporting property. In particular, a substance having a hole mobility of $1\times10^{-6}$ cm$^2$/Vs or higher is preferably used for forming the hole-transporting layer. Note that the substance having a high hole-transporting property is a substance of which the hole mobility is higher than the electron mobility and a ratio of the hole mobility to the electron mobility (i.e., the hole mobility/the electron mobility) is more than 100. As a specific example of a substance that can be used for forming the hole-transporting layer 312, 4,4'-bis[N-(1-naphthyl)-N-phenylamino]biphenyl (abbreviation: NPB), 4,4'-bis[N-(3-methylphenyl)-N-phenylamino]biphenyl (abbreviation: TPD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis{N-[4-(N,N-di-m-tolylamino)phenyl]-N-phenylamino}biphenyl (abbreviation: DNTPD), 1,3,5-tris[N,N-di(m-tolyl)amino]benzene (abbreviation: m-MMDAB), 4,4',4"-tris(N-carbazolyl)triphenylamine (abbreviation: TCTA), phthalocyanine (abbreviation: H$_2$Pc), copper phthalocyanine (abbreviation: CuPc), vanadyl phthalocyanine (abbreviation: VOPc), and the like can be given. Further, the hole-transporting layer 312 may be a layer having a multilayer structure that is formed by combining two or more layers formed from the foregoing substances.

Moreover, as shown in FIG. 3, an electron-transporting layer 314 may be provided between the second electrode 302 and the light-emitting layer 313. The electron-transporting layer is a layer having a function of transporting electrons injected from the second electrode 302 to the light-emitting layer 313. Thus, providing the electron-transporting layer 314 makes it possible to isolate the second electrode 302 from the light-emitting layer 313. Consequently, it is possible to prevent light emission from going out due to a metal contained in the second electrode 302. The electron-transporting layer is preferably formed using a substance having a high electron-transporting property. In particular, a substance having an electron mobility of $1\times10^{-6}$ cm$^2$/Vs or higher is preferably used for forming the electron-transporting layer. Note that the substance having a high electron-transporting property is a substance of which the electron mobility is higher than the hole mobility and a ratio of the electron mobility to the hole mobility (i.e., the electron mobility/the hole mobility) is more than 100. As a specific example of a substance that can be used for forming the electron-transporting layer 314, a metal complex such as tris(8-quinolinolato) aluminum (abbreviation: Alq), tris(4-methyl-8-quinolinolato) aluminum (abbreviation: Almq$_3$), bis(10-hydroxybenzo[h]-quinolinato) beryllium (abbreviation: BeBq$_2$), bis(2-methyl-8-quinolinolato)-4-phenylphenolato-aluminum (abbreviation: BAlq), bis[2-(2-hydroxyphenyl)benzoxazolato]zinc (abbreviation: Zn(BOX)$_2$), and bis[2-(2-hydroxyphenyl)benzothiazolato]zinc (abbreviation: Zn(BTZ)$_2$) can be given. In addition, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), 4,4-bis(5-methylbenzoxazole-2-yl)stilbene (abbreviation: BzOs), and the like can be given. Further, the electron-transporting layer 314 may be a layer having a multilayer structure that is formed by combining two or more layers formed from the foregoing substances.

Each of the hole-transporting layer 312 and the electron-transporting layer 314 may be formed using a bipolar substance, in addition to the foregoing substances. The bipolar substance is a substance of which a ratio of a mobility of one carrier, to that of the other is 100 or less, preferably 10 or less when comparing an electron mobility and a hole mobility. As a bipolar substance, for example, 2,3-bis(4-diphenylaminophenyl)quinoxaline (abbreviation: TPAQn) and the like can be given. Among the bipolar substances, in particular, a substance having a hole and electron mobility of $1\times10^{-6}$ cm$^2$/Vs or higher is preferably used. Also, the hole-transporting layer 312 and the electron-transporting layer 314 may be formed using the same bipolar substance.

As shown in FIG. 3, a hole-injecting layer 311 may also be provided between the first electrode 301 and the hole-transporting layer 312. The hole-injecting layer 311 is a layer having a function of helping injection of holes from the first electrode 301 into the hole-transporting layer 312. Providing the hole-injecting layer 311 makes it possible to reduce the difference in an ionizing potential between the first electrode 301 and the hole-transporting layer 312 so that holes are easily injected. The hole-injecting layer 311 is preferably formed by using a substance of which the ionizing potential is lower than that of a substance contained in the hole-transporting layer 312 and higher than that of a substance contained in the first electrode 301, or a substance in which an energy band is bent when provided as a thin film with a thickness of 1 to 2 nm between the hole-transporting layer 312 and the first electrode 301. As a specific example of a substance that can be used for forming the hole-injecting layer 311, phthalocyanine (abbreviation: H$_2$Pc) and a phthalocyanine compound such as copper phthalocyanine (CuPc), a high molecular compound such as a poly(ethylene dioxythiophene)/poly(styrene sulfonate) aqueous solution (PEDOT/PSS), or the like can be given.

That is, the hole-injecting layer 311 can be formed by using a substance selected from among substances having hole-transporting properties so that the ionizing potential of the hole-injecting layer 311 is relatively lower than that of the hole-transporting layer 312. Note that, in the case of providing the hole-injecting layer 311, the first electrode 301 is preferably formed using a substance having a high work function, such as indium tin oxide.

An electron-injecting layer 315 may also be provided between the second electrode 302 and the electron-transporting layer 314 as shown in FIG. 3. The electron-injecting layer 315 is a layer having a function of helping injection of electrons from the second electrode 302 into the electron-transporting layer 314. Providing the electron-injecting layer 315 makes it possible to reduce the difference in electron affinity between the second electrode 302 and the electron-transporting layer 314 so that electrons are easily injected. The electron-injecting layer 315 is preferably formed using a substance of which the electron affinity is higher than a substance contained in the electron-transporting layer 314 and lower than a substance contained in the second electrode 302, or a substance of which an energy band is bent when provided as a thin film with a thickness of 1 to 2 nm between the electron-transporting layer 314 and the second electrode 302. As a specific example of a substance that can be used for forming the electron-injecting layer 315, an inorganic material such as alkali metal, alkaline earth metal, fluoride of alkali metal, fluoride of alkaline earth metal, alkali metal oxide, or alkaline earth metal oxide can be given. In addition to the inorganic material, the substances which can be used for forming the electron-transporting layer 314, such as BPhen, BCP, p-EtTAZ, TAZ, and BzOs, can also be used as a substance for forming the electron-injecting layer 315 by selecting from among these substances a substance having higher electron affinity than a substance used for forming the electron-transporting layer 314. That is, a substance where electron affinity of the electron-injecting layer 315 is relatively higher than that of the electron-transporting layer 314 is selected from substances having electron-transporting properties, so that the electron-injecting layer 315 can be formed. Further, in the case of providing the electron-injecting layer 315, the first electrode 301 is preferably formed using a substance having a low work function, such as aluminum.

In the light-emitting element of the present invention as described above, each of the hole-injecting layer 311, the hole-transporting layer 312, the light-emitting layer 313, the electron-transporting layer 314, and the electron-injecting layer 315 may be formed by any method, such as an evaporation method, an inkjet method, or a coating method. Note that each of the first electrode 301 and the second electrode 302 may be formed by any method, such as a sputtering method or an evaporation method.

Moreover, a hole-generating layer may be provided instead of the hole-injecting layer 311. An electron-generating layer may be provided instead of the electron-injecting layer 315.

The hole-generating layer is a layer which generates holes. The hole-generating layer can be formed by mixing at least one substance selected from substances of which a hole mobility is higher than an electron mobility and bipolar substances, and a substance exhibiting an electron-accepting property with respect to the selected substance. As the substance of which a hole mobility is higher than an electron mobility, a similar substance to the substance that can be used for forming the hole-transporting layer 312 can be used. As the bipolar substance, a bipolar substance such as TPAQn can be used. Moreover, among substances having a higher hole mobility than an electron mobility and bipolar substances, in particular, a substance having triphenylamine in a skeleton is preferably used. Using the substance having triphenylamine in the skeleton makes it possible to generate holes easily. As the substance exhibiting an electron-accepting property, metal oxide such as molybdenum oxide, vanadium oxide, ruthenium oxide, or rhenium oxide is preferably used.

Note that, the electron-generating layer is a layer generating electrons. The electron-generating layer can also be formed by mixing at least one substance selected from substances of which a hole mobility is higher than an electron mobility and bipolar substances, and a substance exhibiting an electron-donating property with respect to the selected substance. As the substance of which the electron mobility is higher than the hole mobility, a similar substance to a substance that can be used for forming the electron-transporting layer 314 can be used. As the bipolar substance, the foregoing bipolar substance such as TPAQn can be used. As the substance exhibiting an electron-donating property, a substance selected from alkali metal and alkaline earth metal, specifically lithium (Li), calcium (Ca), sodium (Na), potassium (K), magnesium (Mg), or the like can be used. Moreover, a substance selected from alkali metal oxide, alkaline earth metal oxide, alkali metal nitride, alkaline earth metal nitride, specifically, lithium oxide ($Li_2O$), calcium oxide (CaO), sodium oxide ($Na_2O$), potassium oxide ($K_2O$), and magnesium oxide (MgO), lithium fluoride (LiF), cesium fluoride (CsF), and calcium fluoride ($CaF_2$) can be used as the substance exhibiting an electron-donating property.

A light-emitting element of the present invention having the foregoing structure is manufactured by using a material which is manufactured through the process of evaluating photochemical stability described in Embodiment Mode 1. Therefore, a change in luminance with light-emitting time is small and the light-emitting element operates favorably.

Embodiment Mode 3

Since a change in luminance with light-emitting time is small in the light-emitting element of the present invention described in Embodiment Mode 2, a light-emitting device capable of displaying an image favorably for a long time can be provided.

In this embodiment mode, a circuit structure and a driving method of a light-emitting device having a display function will be described with reference to FIGS. 4 to 7.

Figure 4:
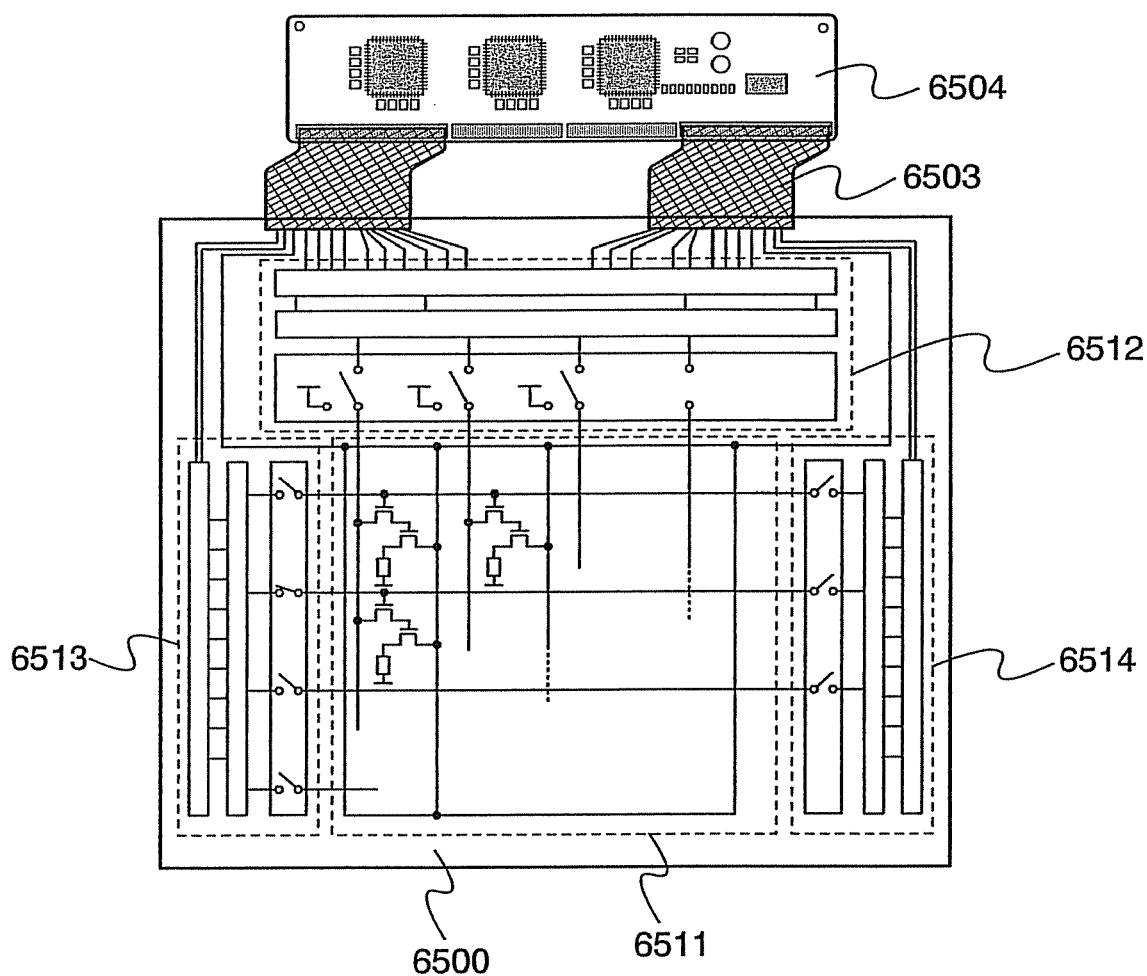
FIG. 4 shows a light-emitting device according to the present invention.

FIG. 4 is a schematic top view of a light-emitting device to which the present invention is applied. In FIG. 4, a pixel portion 6511, a source signal line driver circuit 6512, a writing gate signal line driver circuit 6513, and an erasing gate signal line driver circuit 6514 are provided over a substrate 6500. The source signal line driver circuit 6512, the writing gate signal line driver circuit 6513, and the erasing gate signal line driver circuit 6514 are each connected to an FPC (flexible printed circuit) 6503 which is an external input terminal, through wirings. Each of the source signal line driver circuit 6512, the writing gate signal line driver circuit 6513, and the erasing gate signal line driver circuit 6514 receive video signals, clock signals, start signals, reset signals, and the like from the FPC 6503. The FPC 6503 has a printed wiring board (PWB) 6504 attached thereto. Note that the driver circuit portion is not necessarily formed over the same substrate as the pixel portion 6511 as described above. For example, the driver circuit portion may be provided outside of the substrate by utilizing a TCP in which an IC chip is mounted over an FPC having a wiring pattern, or the like.

A plurality of source signal lines extending in columns are aligned in rows in the pixel portion 6511. In addition, power supply lines are aligned in rows. A plurality of gate signal lines extending in rows are aligned in columns in the pixel portion 6511. In addition, a plurality of sets of circuits each including a light-emitting element are aligned in the pixel portion 6511.

Figure 5:
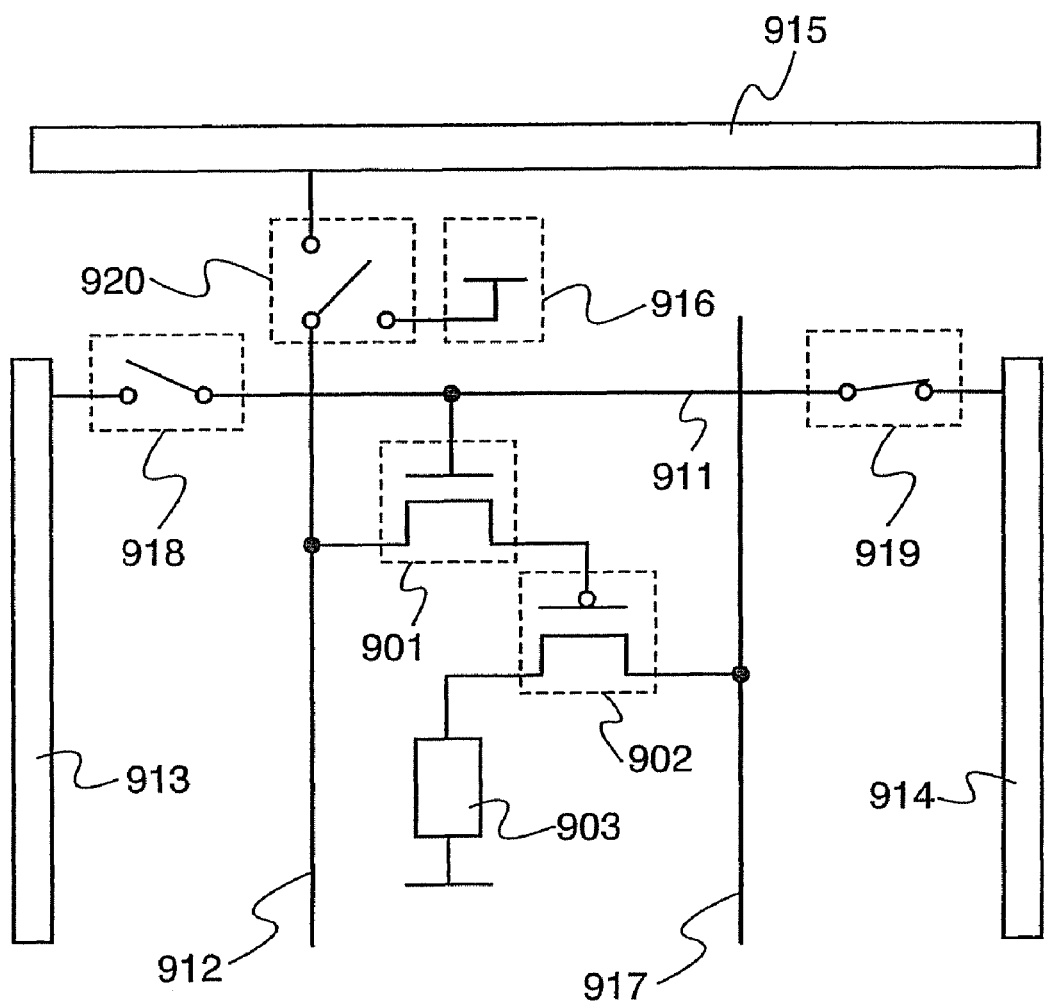
FIG. 5 shows a circuit in a light-emitting device according to the present invention.

FIG. 5 is a diagram showing a circuit for operating one pixel. The circuit shown in FIG. 5 has a first transistor 901, a second transistor 902, and a light-emitting element 903.

Each of the first transistor 901 and the second transistor 902 is a three-terminal element including a gate electrode, a drain region, and a source region. A channel region is interposed between the drain region and the source region. The region serving as the source region and the region serving as the drain region are changed depending on a structure of the transistor, an operational condition, and the like; therefore, it is difficult to determine which region serves as the source region or the drain region. Therefore, in this embodiment mode, the regions serving as the source and the drain are each denoted as a first electrode or a second electrode.

A gate signal line 911 and a writing gate signal line driver circuit 913 are provided to be electrically connected or disconnected to each other by a switch 918. The gate signal line 911 and an erasing gate signal line driver circuit 914 are provided to be electrically connected or disconnected to each other by a switch 919. A source signal line 912 is provided to be electrically connected to either a source signal line driver circuit 915 or a power source 916 by a switch 920. A gate of the first transistor 901 is electrically connected to the gate signal line 911. The first electrode of the first transistor is electrically connected to the source signal line 912 while the second electrode thereof is electrically connected to the gate electrode of the second transistor 902. The first electrode of the second transistor 902 is electrically connected to a current supply line 917 while the second electrode thereof is electrically connected to one electrode included in the light-emitting element 903. Further, the switch 918 may be included in the writing gate signal line driver circuit 913. The switch 919 may also be included in the erasing gate signal line driver circuit 914. In addition, the switch 920 may be included in the source signal line driver circuit 915.

Figure 6:
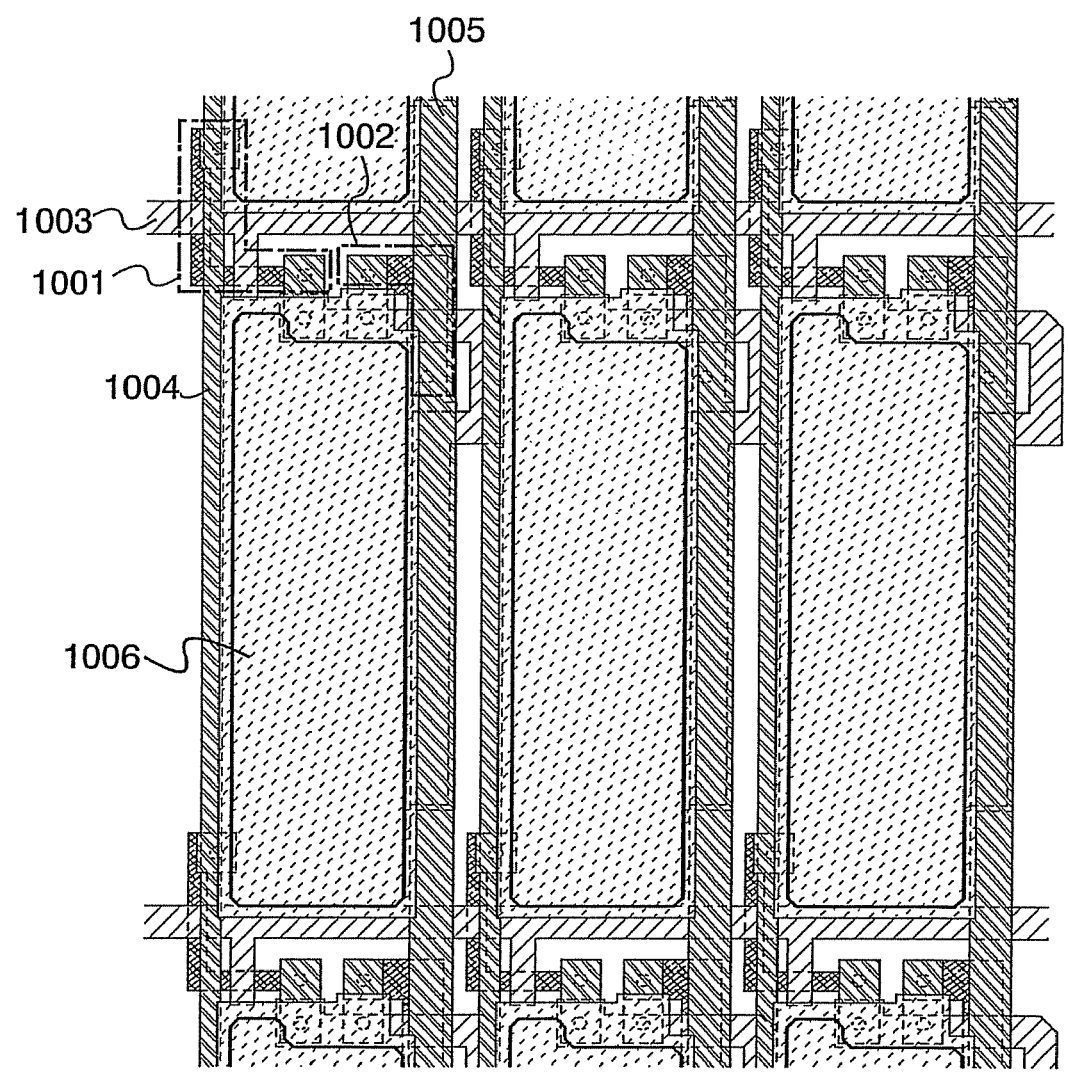
FIG. 6 shows a top view of a light-emitting device according to the present invention.

The arrangement of the transistors, the light-emitting elements, and the like in the pixel portion is not particularly limited. For example, the arrangement shown in a top view of FIG. 6 can be employed. In FIG. 6, a first electrode of a first transistor 1001 is connected to a source signal line 1004 while a second electrode thereof is connected to a gate electrode of a second transistor 1002. A first electrode of the second transistor is connected to a current supply line 1005 and a second electrode thereof is connected to an electrode 1006 of a light-emitting element. A part of the gate signal line 1003 functions as a gate electrode of the first transistor 1001.

Figure 7:
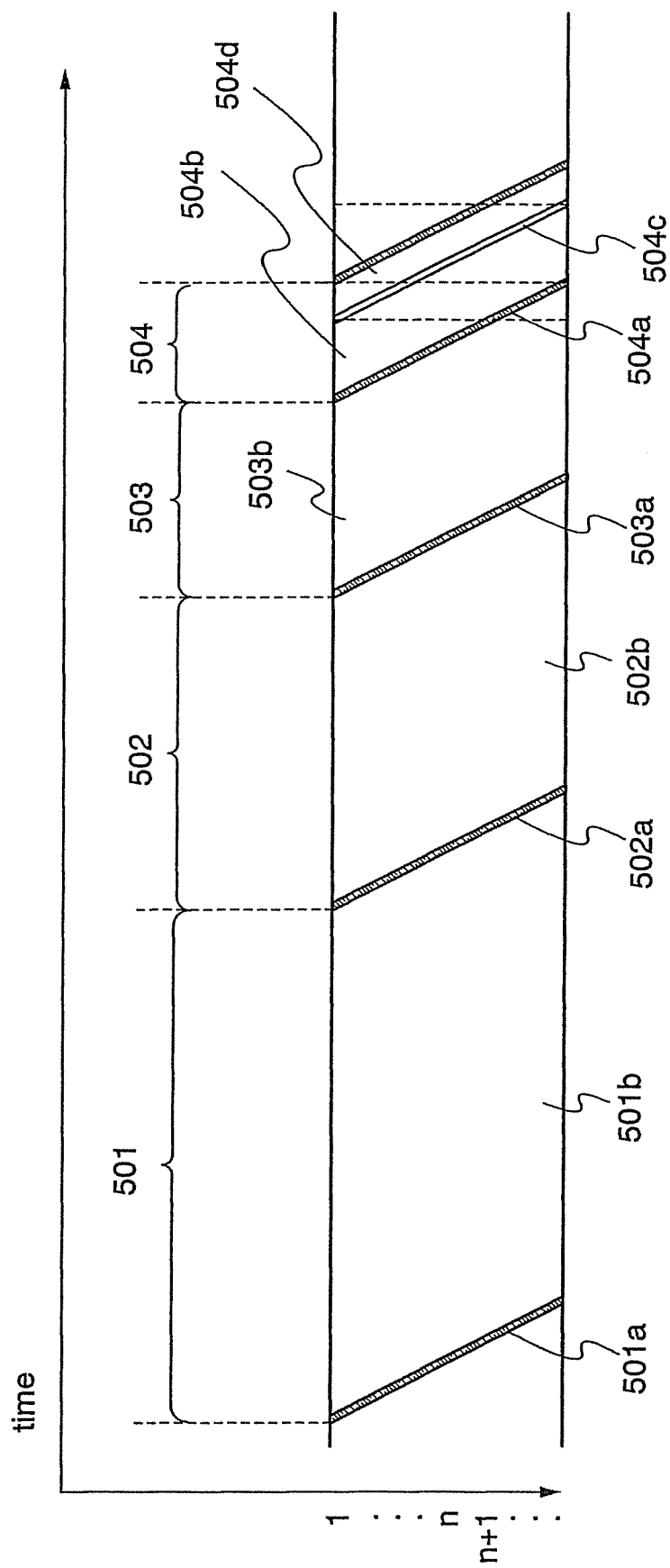
FIG. 7 shows a frame operation of a light-emitting device according to the present invention.

Next, the driving method is described. FIG. 7 is a diagram explaining an operation of a frame with time. In FIG. 7, a horizontal direction indicates time passage while a vertical direction indicates the number of scanning stages of a gate signal line.

When an image is displayed using the light-emitting device of the present invention, a rewriting operation of a screen and a displaying operation are carried out repeatedly during a displaying period. The number of rewriting operations is not particularly limited. However, the rewriting operation is preferably performed at least about 60 times a second so that a person watching a displayed image does not detect flicker. A period of performing the rewriting operation and the displaying operation of one image (one frame) is herein referred to as one frame period.

As shown in FIG. 7, one frame is time divided into four sub-frames 501, 502, 503, and 504, which include writing periods 501a, 502a, 503a, and 504a and holding periods 501b, 502b, 503b, and 504b, respectively. The light-emitting element to which a signal for emitting light has been applied emits light during the holding periods. The length ratio of the holding periods in the sub-frames satisfies the first sub-frame 501: the second sub-frame 502: the third sub-frame 503: the fourth sub-frame $504=2^3:2^2:2^1:2^0=8:4:2:1$. This allows the light-emitting device to exhibit 4-bit gray scale. Further, the number of bits and the number of gray scales are not limited to those shown in this embodiment mode. For instance, one frame may be divided into eight sub-frames so as to achieve 8-bit gray scale.

The operation in one frame is described. In the sub-frame 501, the writing operation is performed in first to last rows, sequentially. Therefore, the starting time of the writing period is different in each row. The holding period 501b starts sequentially in the row in which the writing period 501a has been terminated. In the holding period 501b, a light-emitting element to which a signal for emitting light has been applied remains in a light-emitting state. The sub-frame 501 is changed to the next sub-frame 502 sequentially in the row in which the holding period 501b has been terminated. In the sub-frame 502, a writing operation is sequentially performed in the first to last rows in the same manner as that of the sub-frame 501. The above-mentioned operations are carried out repeatedly up to the holding period 504b of the sub-frame 504. After terminating the operation in the sub-frame 504, an operation in the next frame starts. Accordingly, the sum of light-emitting periods in the respective sub-frames corresponds to the light-emitting period of each light-emitting element in one frame. By changing the light-emitting period for each light-emitting element and combining such light-emitting periods variously within one pixel, various display colors with different brightness and chromaticity can be obtained.

When the holding period is intended to be forcibly terminated in the row in which the writing period has already been terminated, and the holding period has started prior to terminating the writing operation up to the last row as shown in the sub-frame 504, an erasing period 504c is preferably provided after the holding period 504b so as to stop light emission forcibly. The row where light emission is forcibly terminated does not emit light for a certain period (this period is referred to as a non light-emitting period 504d). Upon terminating the writing period in the last row, a writing period of a next sub-frame (or, a next frame) starts sequentially from the first row. This can prevent the writing period in the sub-frame 504 from superposing with the writing period in the next sub-frame.

Although the sub-frames 501 to 504 are arranged in an order from the longest holding period in this embodiment mode, they do not necessarily have to be arranged in this order. For example, the sub-frames may be arranged in an order from the shortest holding period. Alternatively, the sub-frames may be arranged randomly. In addition, these sub-frames may further be divided into a plurality of frames. That is, scanning of gate signal lines may be performed a plurality of times during a period of applying the same video signal.

The operations of the circuit shown in FIG. 5 in the writing period and the erasing period are described below.

The operation in the writing period is described first. In the writing period, the gate signal line 911 in the n-th row (n is a natural number) is electrically connected to the writing gate signal line driver circuit 913 via the switch 918 and is electrically disconnected from the erasing gate signal line driver circuit 914. The source signal line 912 is electrically connected to the source signal line driver circuit via the switch 920. In this case, a signal is inputted to a gate of the first transistor 901 connected to the gate signal line 911 in the n-th row (n is a natural number), thereby turning on the first transistor 901. At this moment, video signals are simultaneously inputted to the source signal lines in the first to last columns. Note that the video signals inputted from the source signal line 912 to the respective columns are independent from each other. The video signal inputted from the source signal line 912 is inputted to a gate electrode of the second transistor 902 via the first transistor 901 connected to each source signal line. Whether the light-emitting element 903 emits light or not is decided depending on a current value of the second transistor 902. For example, when the second transistor 902 is a P-channel type, the light-emitting element 903 emits light by inputting a low level signal to the gate electrode of the second transistor 902. On the other hand, when the second transistor 902 is an N-channel type, the light-emitting element 903 emits light by inputting a high level signal to the gate electrode of the second transistor 902.

Next, the operation in the erasing period is described. In the erasing period, the gate signal line 911 in the n-th row (n is a natural number) is electrically connected to the erasing gate signal line driver circuit 914 via the switch 919 and is electrically disconnected from the writing gate signal line driver circuit 913. The source signal, line 912 is electrically connected to the power source 916 via the switch 920. In this case, a signal is inputted to the gate of the first transistor 901, which is connected to the gate signal line 911 in the n-th row, whereby the first transistor 901 is turned on. At this time, erasing signals are simultaneously inputted to the source signal lines of the first to last columns. The erasing signal inputted from the source signal line 912 is inputted to the gate electrode of the second transistor 902 via the first transistor 901, which is connected to each source signal line. A supply of current flowing from the current supply line 917 to the light-emitting element 903 is interrupted by the signal inputted to the second transistor 902. This prevents light from being forcibly emitted by the light emitting element 903. For example, when the second transistor 902 is a P-channel type, the light-emitting element 903 is prevented from emitting light by inputting a high level signal to the gate electrode of the second transistor 902. On the other hand, when the second transistor 902 is an N-channel type, the light-emitting element 903 is prevented from emitting light by inputting a low level signal in the gate electrode of the second transistor 902.

Further, in the erasing period, a signal for erasing is inputted to the n-th row (n is a natural number) by the foregoing operation. However, as mentioned above, the n-th row sometimes remains in the erasing period while another row (e.g., an m-th row (m is a natural number)) remains in the writing period. In this case, since it is necessary to input a signal for erasing to the n-th row and a signal for writing to the m-th row by utilizing the source signal line in the same column, the operation described below is preferably carried out.

After the light-emitting element 903 in the n-th row achieves a non-light-emitting state by the foregoing operation in the erasing period, the gate signal line and the erasing gate signal line driver circuit 914 are immediately disconnected from each other and the source signal line is connected to the source signal line driver circuit 915 by turning on/off the switch 920. The gate signal line and the writing gate signal line driver circuit 913 are connected to each other while the source signal line and the source signal line driver circuit 915 are connected to each other. A signal is selectively inputted to the signal line in the m-th row from the writing gate signal line driver circuit 913, and the first transistor is turned on while signals for writing are inputted to the source signal lines in the first to last columns from the source signal line driver circuit 915. Whether the light-emitting element in the m-th row emits light or not depends on the inputted signals.

After terminating the writing period in the m-th row as mentioned above, the erasing period immediately starts in the (n+1)th row. Therefore, the gate signal line and the writing gate signal line driver circuit 913 are disconnected from each other while the source signal line is connected to the power source 916 by turning on/off the switch 920. Moreover, the gate signal line and the writing gate signal line driver circuit 913 are disconnected from each other while the gate signal line is connected to the erasing gate signal line driver circuit 914. A signal is selectively inputted to the gate signal line in the (n+1)th row from the erasing gate signal line driver circuit 914 to input the signal for turning on the transistor while an erasing signal is inputted thereto from the power source 916. Upon terminating the erasing period in the (n+1)th row in this manner, the writing period in another row immediately starts. The erasing period and the writing period may be repeated in the same manner until the erasing period of the last row.

Although the writing period in the m-th row is provided between the erasing period in the n-th row and the erasing period of the (n+1)th row in this embodiment mode, the present invention is not limited thereto. The writing period of the m-th row may be provided between the erasing period in the (n−1)th row and the erasing period in the n-th row.

Furthermore, in this embodiment mode, when the non-light-emitting period 504*d* is provided like the sub-frame 504, the operation of disconnecting the erasing gate signal line driver circuit 914 from one gate signal line while connecting the writing gate signal line driver circuit 913 to another gate signal line is carried out repeatedly. This operation may be performed in a frame in which a non-light-emitting period is not particularly provided.

Embodiment Mode 4

An example of a light-emitting device including a light-emitting element of the present invention is described with reference to cross-sectional views of FIGS. 8A to 8C.

Figure 8A:
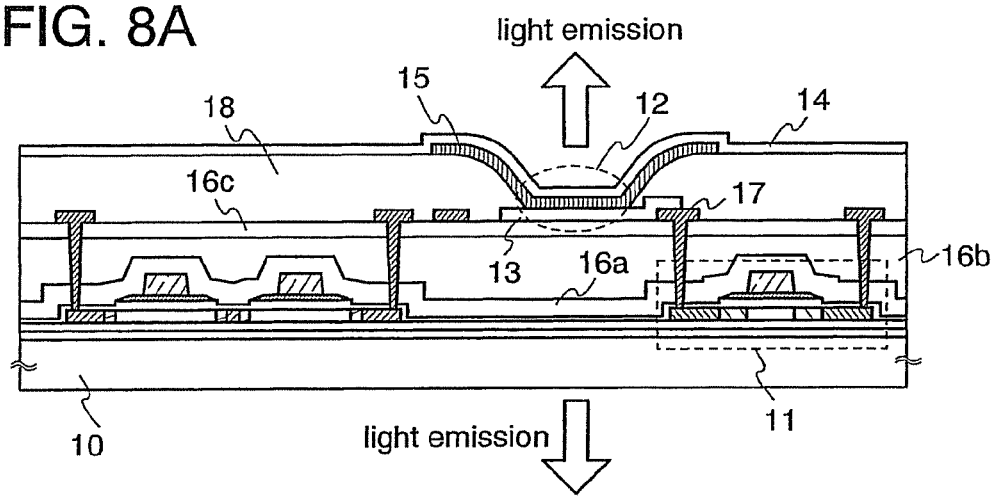
FIGS. 8A to 8C are cross-sectional views of a light-emitting device according to the present invention.
Figure 8B:
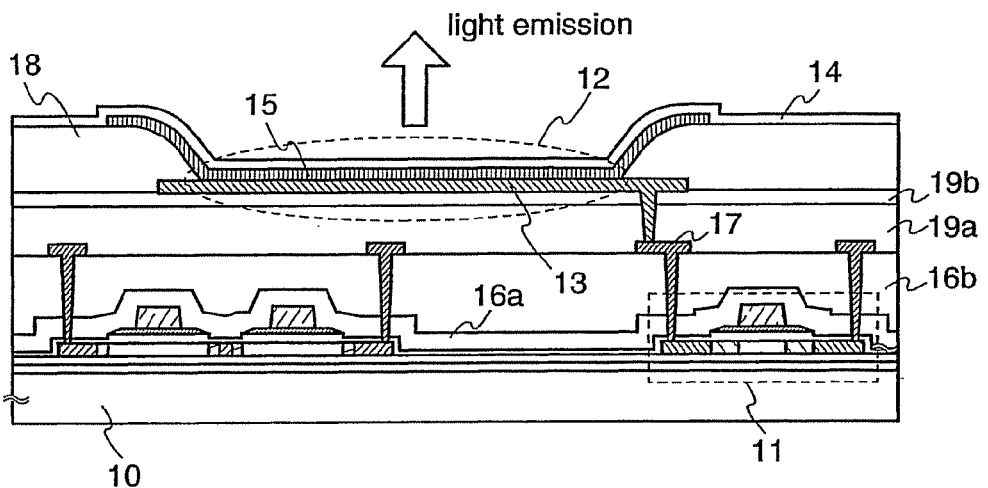
Figure 8C:
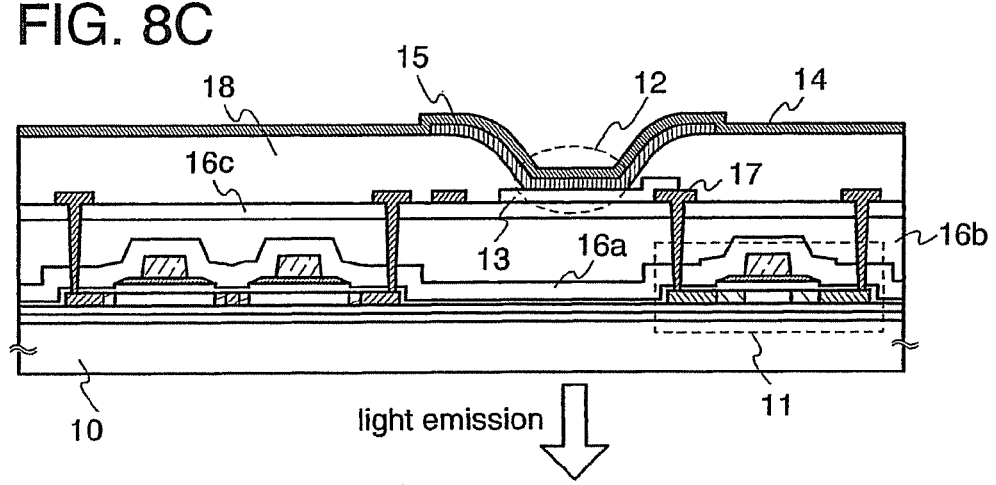

In each of FIGS. 8A to 8C, a transistor 11 provided for driving a light-emitting element 12 of the present invention is surrounded by a dotted line. The light-emitting element 12 of the present invention has a light-emitting layer 15 between a first electrode 13 and a second electrode 14. The light-emitting layer 15 is formed using a light-emitting element material evaluated by the method described in Embodiment Mode 1. A drain of the transistor 11 and the first electrode 13 are electrically connected to each other via a wire 17 that passes through a first interlayer insulating film 16 (16*a*, 16*b*, and 16*c*). The light-emitting element 12 is isolated from another adjacent light-emitting element by a partition wall layer 18. A light-emitting device of the present invention having such a structure is provided over a substrate 10 in this embodiment mode.

Note that the transistor 11 shown in each of FIGS. 8A to 8C is a top-gate type in which a gate electrode is provided over the substrate with a semiconductor layer interposed therebetween. However, the structure of the transistor 11 is not particularly limited thereto, and for example, a bottom-gate type structure may be employed. In the case when the bottom-gate type is employed, either a structure in which a protection film is formed over a semiconductor layer forming a channel (a channel protection type) or a structure in which a semiconductor layer forming a channel is partly depressed (a channel-etched type) may be used.

Furthermore, the semiconductor layer included in the transistor 11 may be formed using any of a crystalline semiconductor, an amorphous semiconductor, a semi-amorphous semiconductor, or the like.

A semi-amorphous semiconductor is described below. The semi-amorphous semiconductor has an intermediate structure between an amorphous structure and a crystalline structure (including a single crystal structure and a polycrystalline structure), and a third condition that is stable in terms of free energy. The semi-amorphous semiconductor further includes a crystalline region having a short range order along with lattice distortion. A crystal grain with a size of 0.5 to 20 nm is included in at least a part of the semi-amorphous semiconductor film. Raman spectrum is shifted to lower wavenumbers than 520 cm$^{-1}$. The diffraction peaks of (111) and (220), which are believed to be derived from a Si crystal lattice, are observed in the semi-amorphous semiconductor by X-ray diffraction. The semi-amorphous semiconductor contains hydrogen or halogen of at least 1 atom % or more for terminating dangling bonds. The semi-amorphous semiconductor is also referred to as a microcrystalline semiconductor. The semi-amorphous semiconductor is formed by glow discharge decomposition (plasma CVD) of silicide gas. As for the silicide gas, $Si_2\mu L$, $SiH_2Cl_2$, $SiHCl_3$, $SiCl_4$, $SiF_4$ or the like can be used in addition to $SiH_4$. The silicide gas may also be diluted with $H_2$, or a mixture of $H_2$ and one or more of rare gas elements selected from He, Ar, Kr, and Ne. The dilution ratio is set to be in the range of 1:2 to 1:1000. The pressure is set to be in the range of approximately 0.1 to 133 Pa. The power frequency is set to be 1 to 120 MHz, preferably 13 to 60 MHz. The substrate heating temperature may be set to be 300° C. or less, more preferably 100 to 250° C. As for impurity elements contained in the film, each concentration of impurities of atmospheric constituents such as oxygen, nitrogen, and carbon is preferably set to be $1\times10^{20}/cm^3$ or less. In particular, the oxygen concentration is set to be $5\times10^{19}/cm^3$ or less, preferably $1\times10^{19}/cm^3$ or less.

As a specific example of a crystalline semiconductor layer, a semiconductor layer formed from single crystal silicon, polycrystalline silicon, silicon germanium, or the like can be given. The crystalline semiconductor layer may be formed by laser crystallization. For example, the crystalline semiconductor layer may be formed by crystallization with use of a solid phase growth method using nickel or the like.

When the semiconductor layer is formed using an amorphous substance such as amorphous silicon, it is preferable that a light-emitting device have circuits including only N-channel transistors as the transistor 11 and other transistors (transistors included in a circuit for driving a light-emitting element). In other cases, a light-emitting device with circuits including either N-channel transistors or P-channel transistors may be employed. Moreover, a light-emitting device with circuits including both an N-channel transistor and a P-channel transistor may be used.

The first interlayer insulating film 16 may include a plurality of layers as shown in FIGS. 8A and 8C, or a single layer. Note that, the first interlayer insulating film 16*a* is formed from an inorganic material such as silicon oxide or silicon nitride. The first interlayer insulating film 16*b* is formed using acrylic, siloxane (which is a compound which has a skeleton structure formed by a silicon (Si)-oxygen (O) bond and includes hydrogen or an alkyl group as its substituent), or a substance with a self-planarizing property such as silicon oxide that can be formed by a coating method. Moreover, the first interlayer insulating film 16*c* is formed with a silicon nitride film containing argon (Ar). Note that the substances contained in the respective layers are not particularly limited thereto. Therefore, substances other than the foregoing substances may be employed. Alternatively, a layer formed using a substance other than the foregoing substances may be additionally provided. Accordingly, the first interlayer insulating film 16 may be formed by using both an inorganic material and an organic material or by using one of an inorganic film or an organic film.

An edge portion of a partition wall layer 18 preferably has a shape in which the radius of curvature is continuously varied. This partition wall layer 18 is formed by using acrylic, siloxane, resist, silicon oxide, or the like. Further, the partition wall layer 18 may be formed using either or both of an inorganic film and an organic film.

Each of FIGS. 8A and 8C shows a structure in which only the first interlayer insulating film 16 is interposed between the transistor 11 and the light-emitting element 12. However, as shown in FIG. 8B, a second interlayer insulting film 19 (19a and 19b) may be provided in addition to the first interlayer insulating film 16 (16a and 16b). In the light-emitting device shown in FIG. 8B, the first electrode 13 passes through the second interlayer insulating film 19 to be connected to the wire 17.

The second interlayer insulating film 19 may include a plurality of layers or may be a single layer like the first interlayer insulating film 16. The second interlayer insulating film 19a is formed using acrylic, siloxane, or a substance with a self-planarizing property such as silicon oxide that can be formed by a coating method. The second interlayer insulating film 19b is formed using a silicon nitride film containing argon (Ar). The substances contained in the respective layers of the second interlayer insulating film are not particularly limited thereto and substances other than the foregoing substances may also be employed. Alternatively, a layer formed from a substance other than the foregoing substances may be additionally provided. Accordingly, the second interlayer insulating film 19 may be formed by using both an inorganic material and an organic material or by using one of an inorganic film or an organic film.

When both the first electrode and the second electrode are formed using a substance with a light-transmitting property in the light-emitting element 12, light generated in the light-emitting element can be taken out through both the first electrode 13 and the second electrode 14 as shown with outline arrows in FIG. 8A. When only the second electrode 14 is formed using a substance with a light-transmitting property, light can be taken out only through the second electrode 14 as shown with an outline arrow in FIG. 8B. In this case, the first electrode 13 is preferably formed using a material with high reflectance, or a film formed using a material with high reflectance (a reflection film) is preferably provided under the first electrode 13. When only the first electrode 13 is formed using a substance with a light-transmitting property, light can be taken out only through the first electrode 13 as shown with an outline arrow in FIG. 8C. In this case, the second electrode 14 is preferably formed using a material with high reflectance or a reflection film is preferably provided over the second electrode 14.

Moreover, the light-emitting element 12 may have a structure in which the first electrode 13 serves as an anode and the second electrode 14 serves as a cathode, or a structure in which the first electrode 13 serves as a cathode and the second electrode 14 serves as an anode. In the former case, the transistor 11 is a P-channel transistor. In the latter case, the transistor 11 is an N-channel transistor.

Embodiment Mode 5

By mounting a light-emitting device of the present invention, an electric appliance can be obtained in which images can be displayed favorably for a long period with less false recognition of information due to disturbance of a displayed image.

Figure 9A:
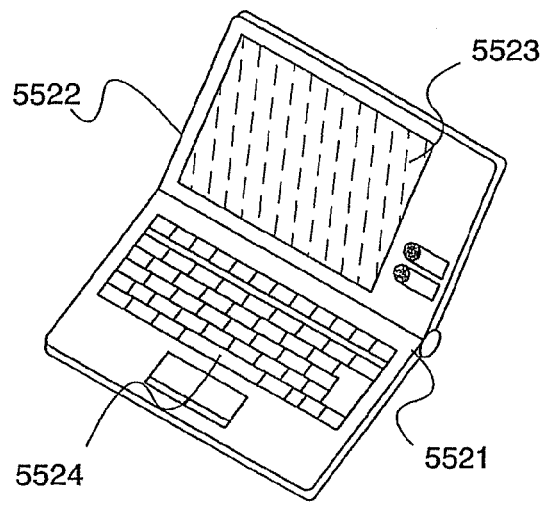
FIGS. 9A to 9C show electric appliances according to the present invention.
Figure 9B:
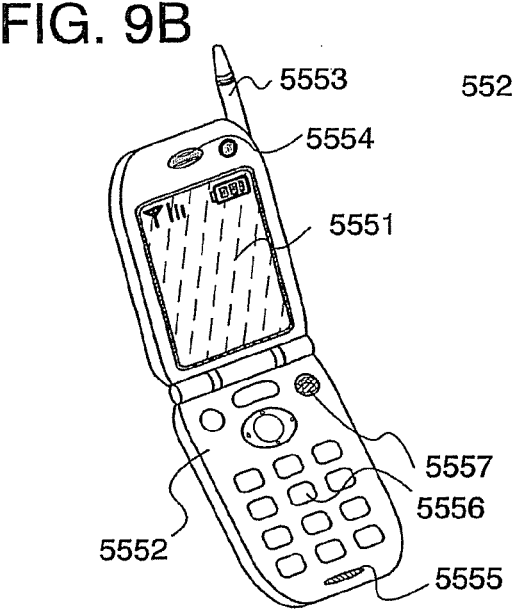
Figure 9C:
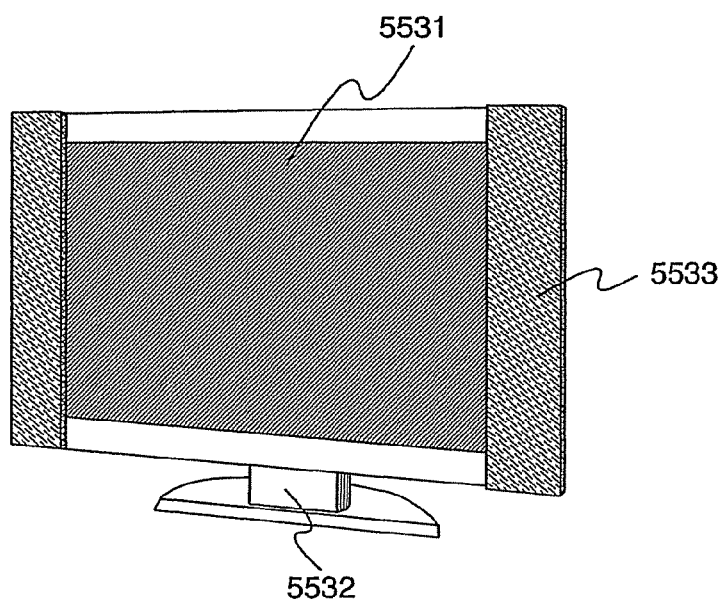

Examples of electric appliances each having a light-emitting device of the present invention mounted are shown in FIGS. 9A to 9C.

FIG. 9A shows a laptop personal computer manufactured according to the present invention, comprising a main body 5521, a housing 5522, a display portion 5523, a keyboard 5524, and the like. By incorporating a light-emitting device having a light-emitting element of the present invention into the display portion, the personal computer can be completed.

FIG. 9B shows a portable phone manufactured according to the present invention, comprising a main body 5552, a display portion 5551, an audio output portion 5554, an audio input portion 5555, operation switches 5556 and 5557, an antenna 5553, and the like. By incorporating a light-emitting device having a light-emitting element of the present invention into the display portion, the portable phone can be completed.

FIG. 9C shows a television receiver manufactured according to the present invention, comprising a display portion 5531, a housing 5532, a speaker 5533, and the like. By incorporating a light-emitting device having a light-emitting element of the present invention into the display portion, the television receiver can be completed.

As described above, a light-emitting device of the present invention is suitable to be used as a display portion of various kinds of electric appliances.

In this embodiment mode, in addition to the electric appliances described above, a light-emitting device having a light-emitting element of the present invention may be mounted on a car navigation system, a camera, a lighting apparatus, and the like.

Embodiment 1

An embodiment in which a light-emitting element material is evaluated by using an evaluation method of a light-emitting element material of the present invention is described.

In this embodiment, each of six kinds of light-emitting element materials, that is, 2-tert-butyl-9,10-di(2-naphthyl) anthracene (abbreviation: t-BuDNA) tris(8-quinolinolato) aluminum (abbreviation: Alq), coumarin 6, 9,10-bis{4-[N-(4-diphenylamino)phenyl-N-phenyl]aminophenyl}-2-tert-butylanthracen e (abbreviation: DPABPA), 9,10-bis{4-[N—(N-phenyl-3-carbazolyl)-N-phenyl]aminophenyl}-2-tert-butylanthracene (abbreviation: PCABPA), 9-[4-(N-carbazolyl)]phenyl-10-phenylanthracene (abbreviation: CzPA) were evaluated.

[t-BuDNA] Sample 1 is a quartz substrate provided with a film formed from 2-tert-butyl-9,10-di(2-naphthyl)anthracene. The following is a detailed description of a manufacturing method and a measurement method of the sample.

The sample 1 was formed by forming a film of 2-tert-butyl-9,10-di(2-naphthyl)anthracene (abbreviation: t-BuDNA) by a vacuum evaporation method using resistance heating over the quartz substrate to have a thickness of 250 nm. The substrate was irradiated with light from a high-pressure mercury lamp (manufactured by Irie Corporation, 400 W high-pressure mercury lamp, H-400P) through a glass filter in a nitrogen atmosphere. The distance between the lamp and the quartz substrate was set to be 20 cm.

Figure 10:
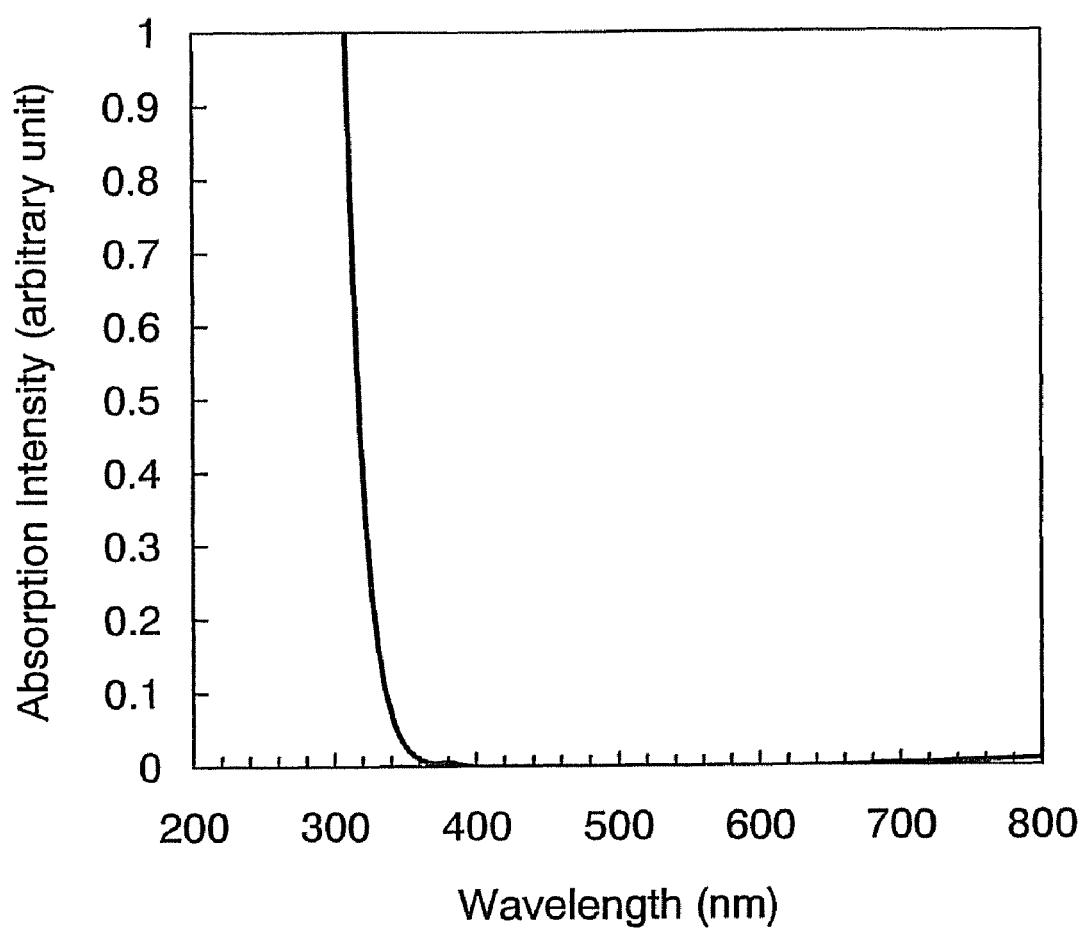
FIG. 10 is a graph showing an UV-visible light absorption spectrum of a glass filter.

FIG. 10 shows an W-visible light absorption spectrum of the glass filter. As shown in FIG. 10, in this experiment, the sample 1 was irradiated with light with a wavelength of more than 320 nm from which a wavelength of less than 320 nm was removed.

Figure 11:
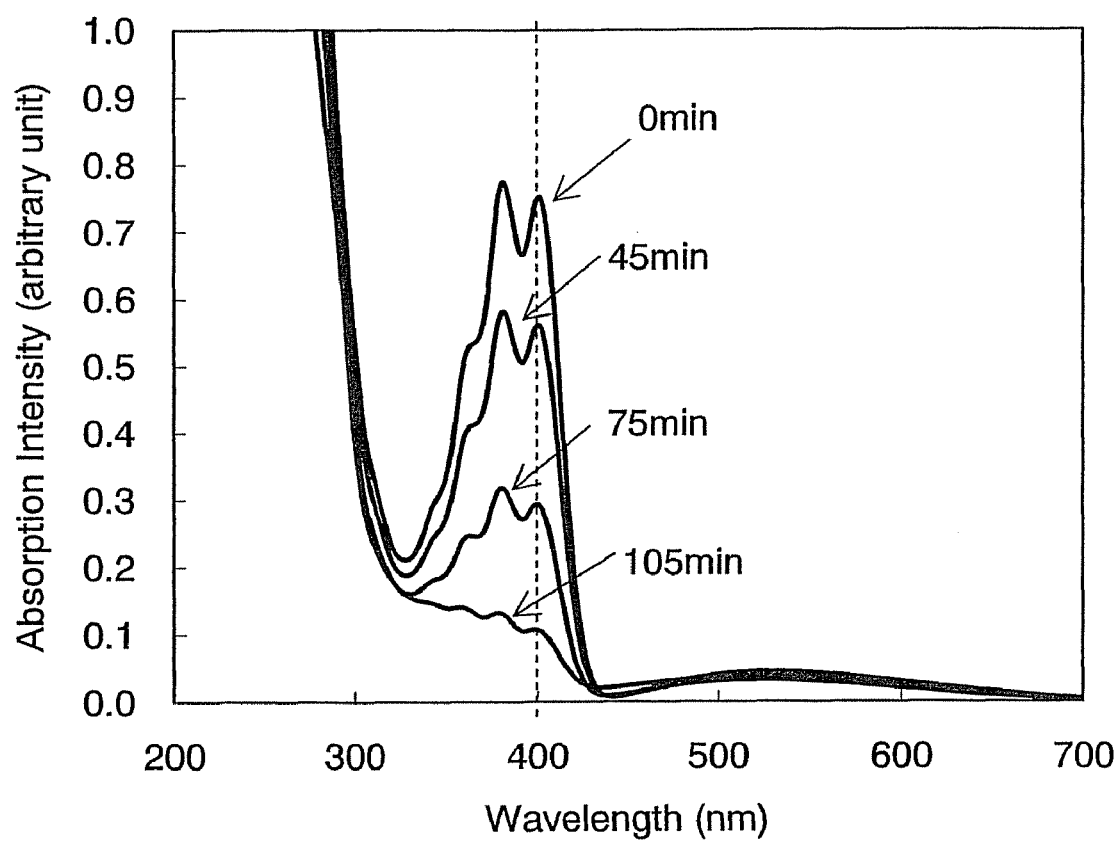
FIG. 11 is a graph showing a change in an absorption spectrum with time.
Figure 12:
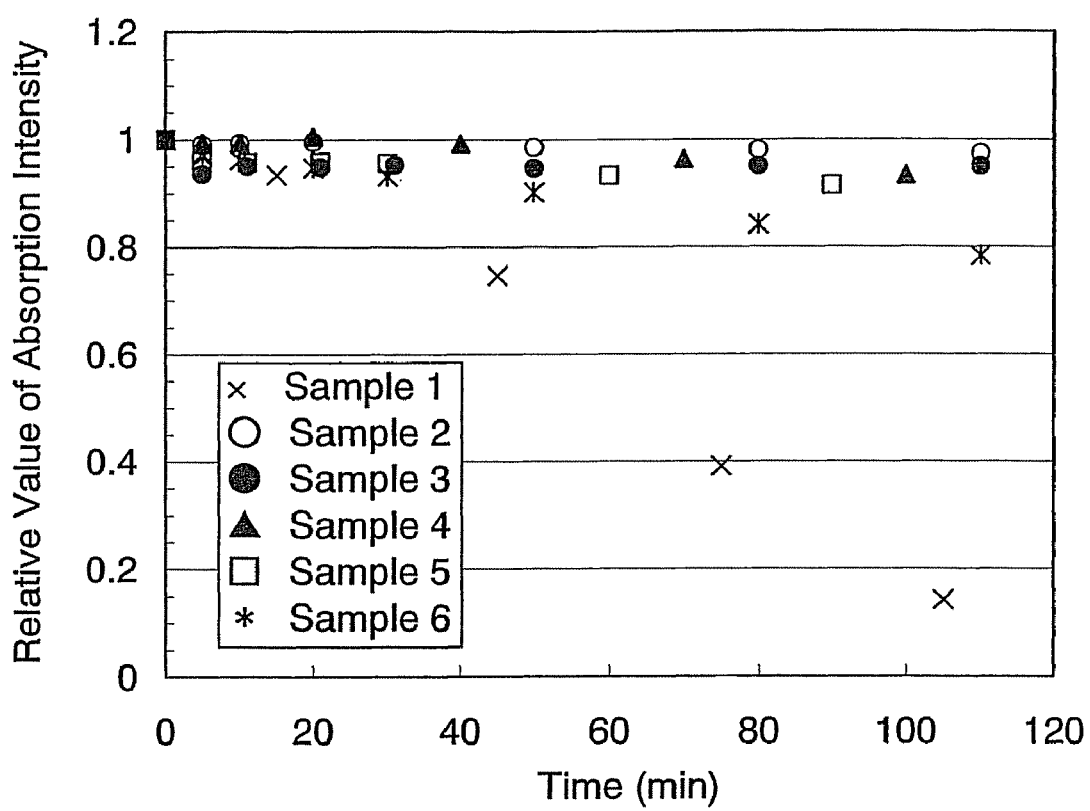
FIG. 12 is a graph showing a change in absorption intensity with time.

After irradiating the sample 1 with light from the high-pressure mercury lamp, for a certain period of time, an absorption spectrum of a t-BuDNA single layer film was measured. By repeating this step, a change in the absorption spectrum of the t-BuDNA single layer film with time was monitored. The result is shown in FIG. 11. In FIG. 11, the horizontal axis indicates a wavelength (nm), and the vertical axis indicates absorption intensity (arbitrary unit). In FIG. 11, absorption observed in a wavelength of about 320 to 420 nm is caused by an anthracene skeleton. The absorption intensity of the wavelength became smaller in association with accumulation of light-irradiation time, which suggests that the anthracene skeleton had disappeared. A change in absorption intensity for a wavelength component of 400 nm with time is plotted (x-mark) in FIG. 12. In FIG. 12, the horizontal axis indicates time (min), and the vertical axis indicates a relative value (arbitrary unit) of absorption intensity at each time of measurement to that of the initial state. As shown in FIG. 12, in this experiment, approximately 80% of absorption caused by an anthracene skeleton was lost by 100 minutes of light irradiation, which suggests that t-BuDNA is photochemically unstable and when t-BuDNA is in the excited state, a side reaction such as decomposition may occur. Note that in FIG. 11, an absorption spectrum of each case where the sum of time in which stress was applied is 0 min (the initial state in which stress of light irradiation is not applied), 45 min, 75 min, and 105 min, while FIG. 12 shows absorption intensity at other times.

Figure 13A:
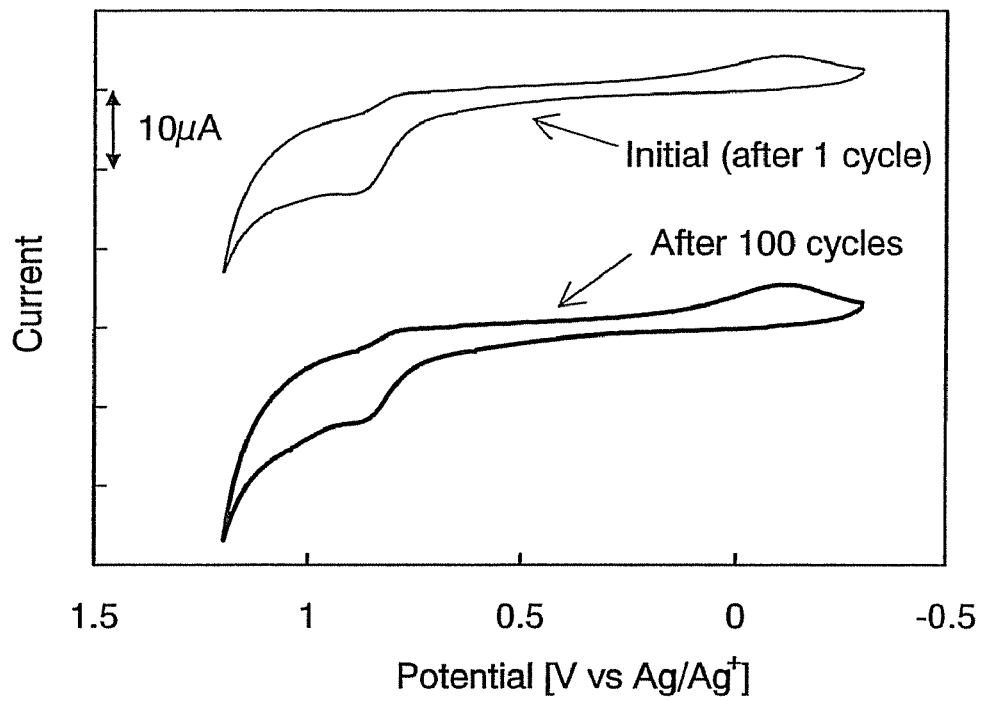
FIGS. 13A and 13B are graphs showing an oxidation reaction characteristic and a reduction reaction characteristic measured by cyclic voltammetry (CV) measurement.
Figure 13B:
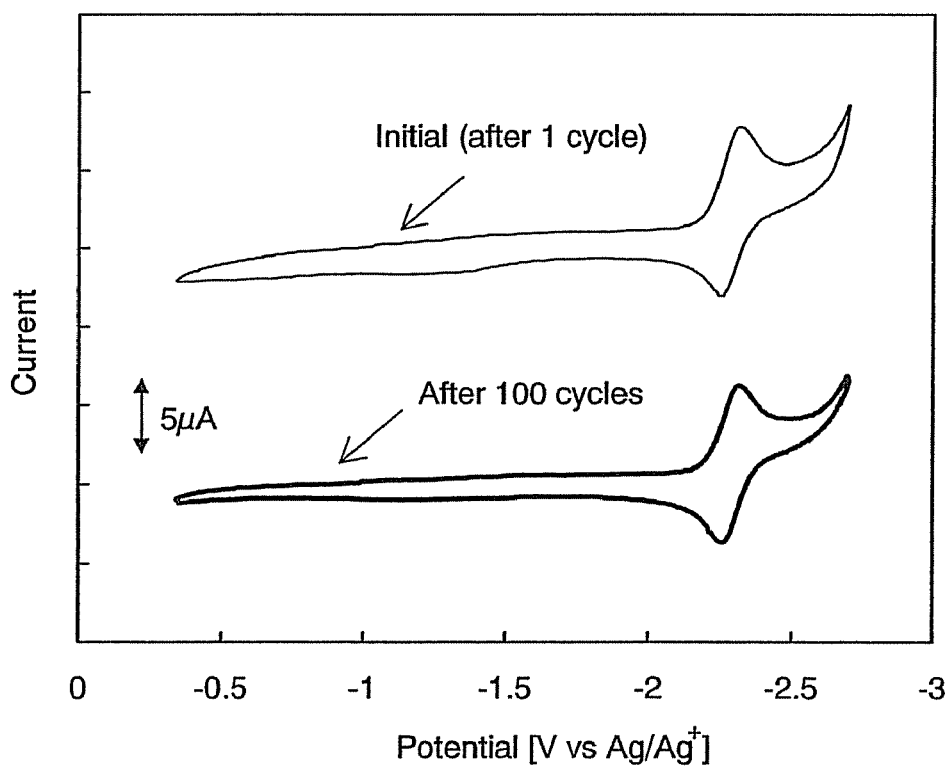

In addition, electrochemical stability of t-BuDNA was examined by a cyclic voltammetry (CV) measurement. Note that in the measurement, an electrochemical analyzer (manufactured by BAS Inc., ALS model 600A) was used. When one cycle includes scanning for changing an electrical potential of a working electrode with respect to a reference electrode from a lower electrical potential to a higher electrical potential, and then changing the electrical potential of the working electrode with respect to the reference electrode from the higher electrical potential to the lower electrical potential, 100 cycles were measured and thereby an oxidation reaction characteristic of t-BuDNA was measured. On the other hand, when one cycle includes scanning for changing the electrical potential of the working electrode to the reference electrode from the higher electrical potential to the lower electrical potential, and then changing the electrical potential of the working electrode to the reference electrode from the lower electrical potential to the higher electrical potential, 100 cycles were measured and thereby a reduction reaction characteristic of t-BuDNA was measured. The oxidation reaction characteristic of t-BuDNA is shown in FIG. 13A and the reduction reaction characteristic of t-BuDNA is shown in FIG. 13B. In FIGS. 13A and 13B, each of the horizontal axes indicates an electrical potential (V) of the working electrode with respect to the reference electrode, and each of the vertical axes indicates an amount of current flowing between the working electrode and an auxiliary electrode.

Figure 14:
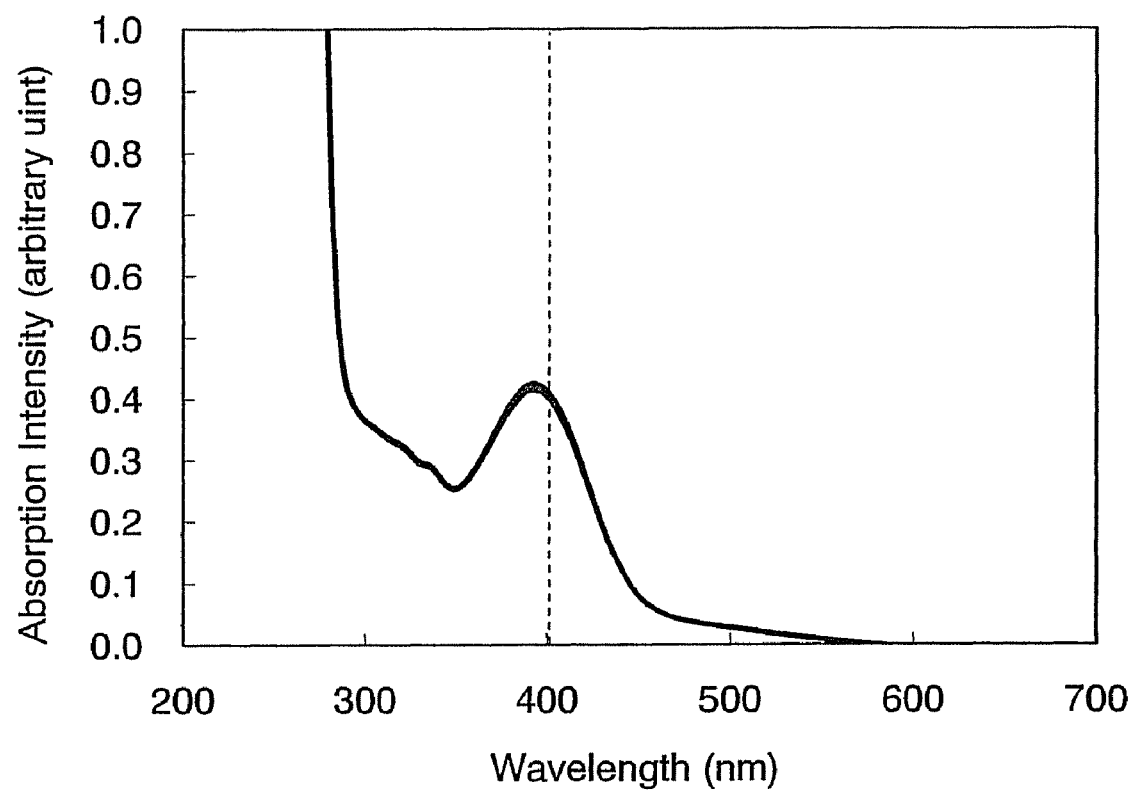
FIG. 14 is a graph showing a change in an absorption spectrum with time.
Figure 15A:
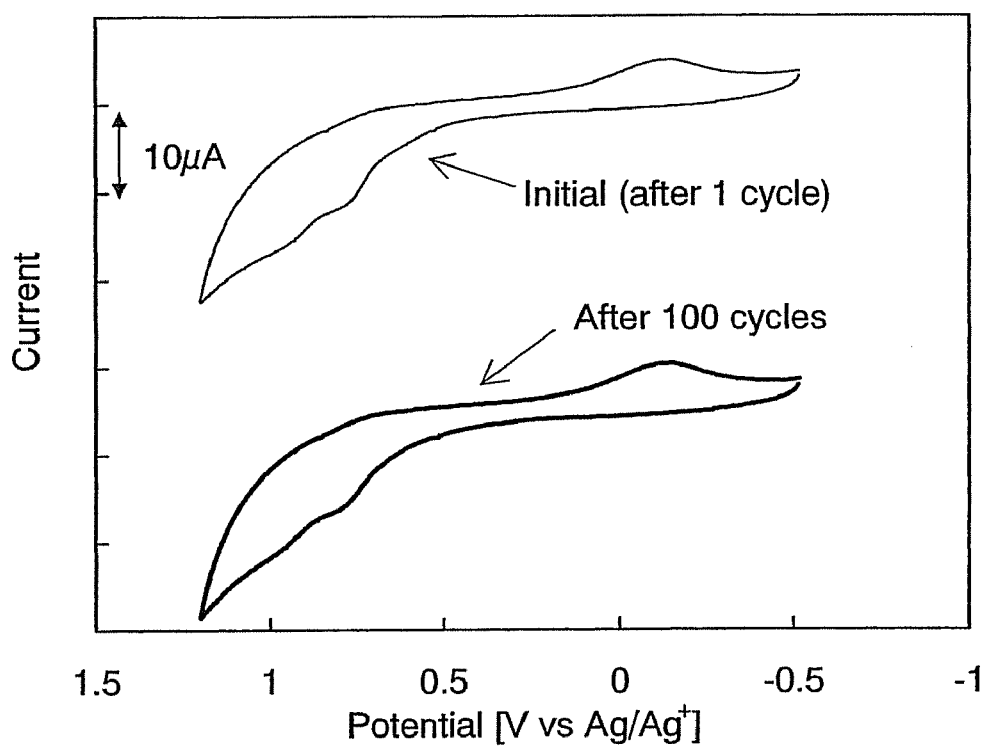
FIGS. 15A and 15B are graphs showing an oxidation reaction characteristic and a reduction reaction characteristic measured by cyclic voltammetry (CV) measurement.
Figure 15B:
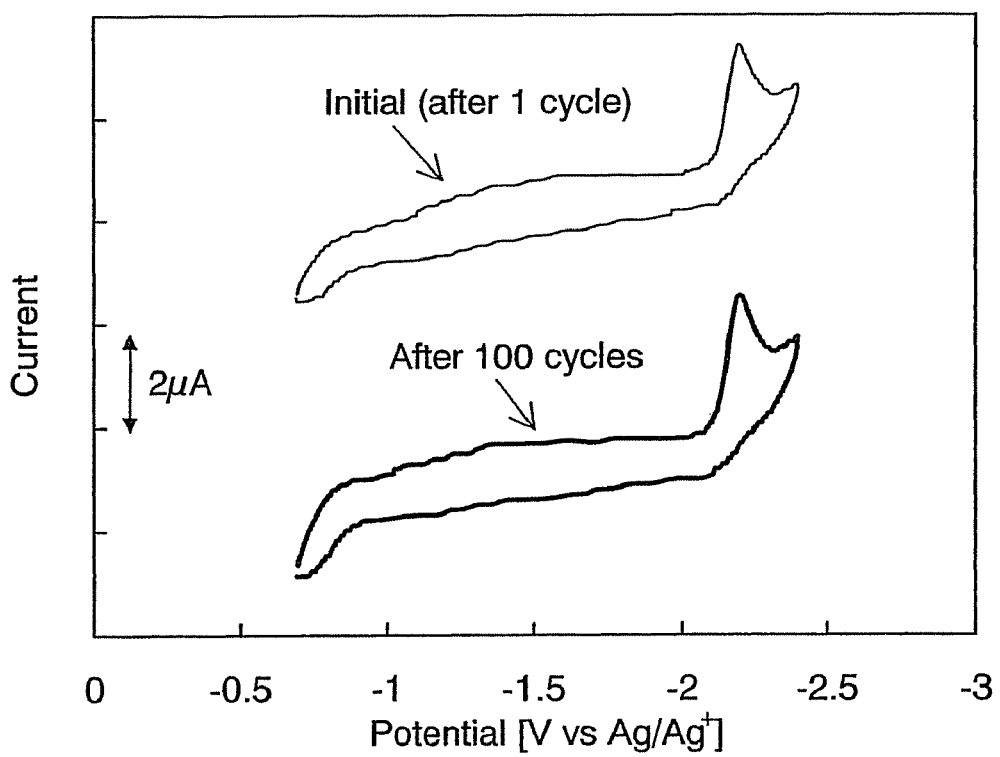

[Alq] Sample 2 is a quartz substrate provided with a film formed from Alq. The sample 2 was formed by a similar method to that of the sample 1 except for using Alq instead of t-BuDNA. Then, photochemical stability of the sample 2 was examined by a similar method to that of the sample 1. FIG. 14 is a graph showing an examination result in which a change in an absorption spectrum of the sample 2 with time was monitored. As shown in FIG. 14, little change was observed in an absorption spectrum of the sample 2 with light-irradiation time, which suggests that Alq is extremely stable in terms of photochemical stability. Note that in FIG. 14, an absorption spectrum of each case where the sum of time in which stress was applied is 0 min, 5 min, 10 min, 20 min, 50 min, 80 min, and 110 min (7 absorption spectra in total) are shown, although they look like one spectrum by overlapping each other. A change in absorption intensity of the sample 2 for a wavelength component of 400 nm with time is plotted (○-mark) in FIG. 12. In addition, electrochemical stability of Alq was also examined. An oxidation reaction characteristic of Alq is shown in FIG. 15A and a reduction reaction characteristic of Alq is shown in FIG. 15B. In FIGS. 15A and 15B, each of the horizontal axes indicates an electrical potential (V) of a working electrode with respect to a reference electrode, and each of the vertical axes indicates an amount of current flowing between the working electrode and an auxiliary electrode.

Figure 16A:
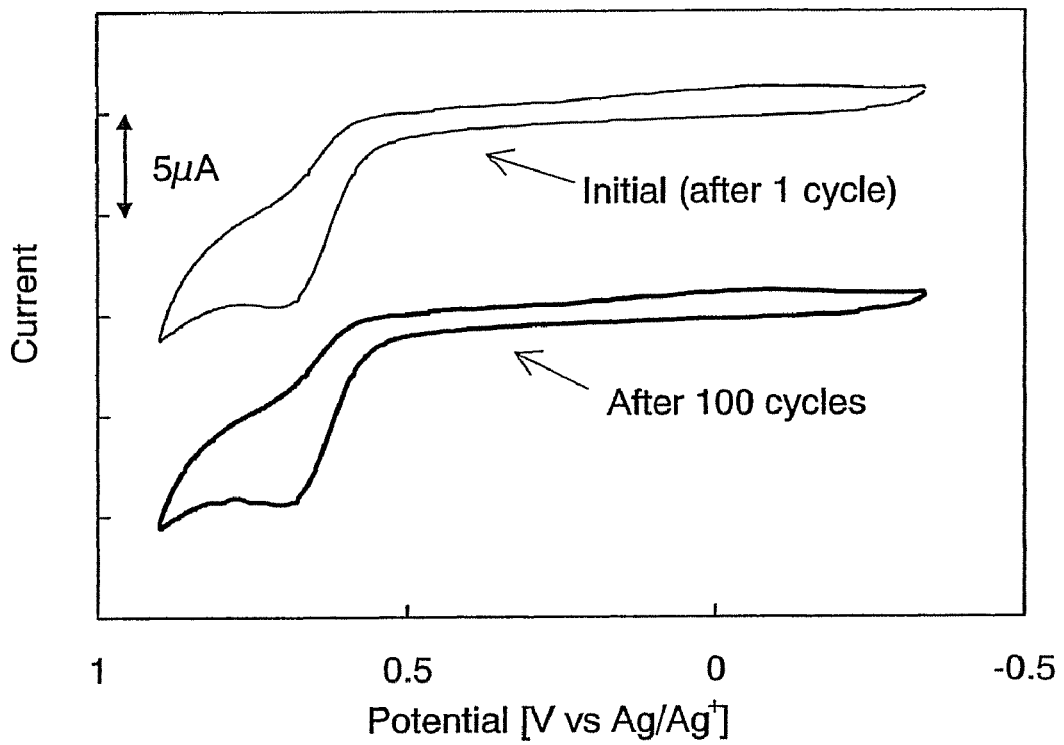
FIGS. 16A and 16B are graphs showing an oxidation reaction characteristic and a reduction reaction characteristic measured by cyclic voltammetry (CV) measurement.
Figure 16B:
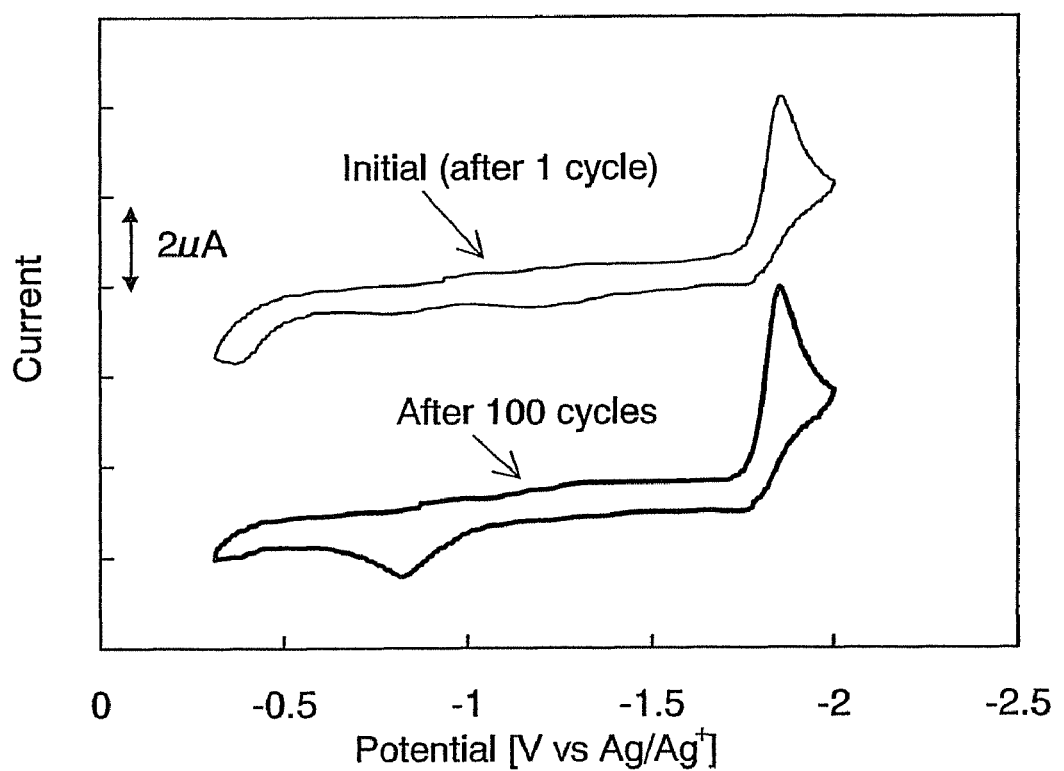

[coumarin 6] Sample 3 is a quartz substrate provided with a film formed from coumarin 6. The sample 3 was formed by a similar method to that of the sample 1 except for using coumarin 6 instead of t-BuDNA. Then, photochemical stability of the sample 3 was examined by a similar method to that of the sample 1. A change in absorption intensity of the sample 3 for a wavelength component of 400 nm with time is plotted (●-mark) in FIG. 12. In addition, electrochemical stability of coumarin 6 was also examined. An oxidation reaction characteristic of coumarin 6 is shown in FIG. 16A and a reduction reaction characteristic of coumarin 6 is shown in FIG. 16B. In FIGS. 16A and 16B, each of the horizontal axes indicates an electrical potential (V) of a working electrode with respect to a reference electrode, and each of the vertical axes indicates an amount of current flowing between the working electrode and an auxiliary electrode.

Figure 17A:
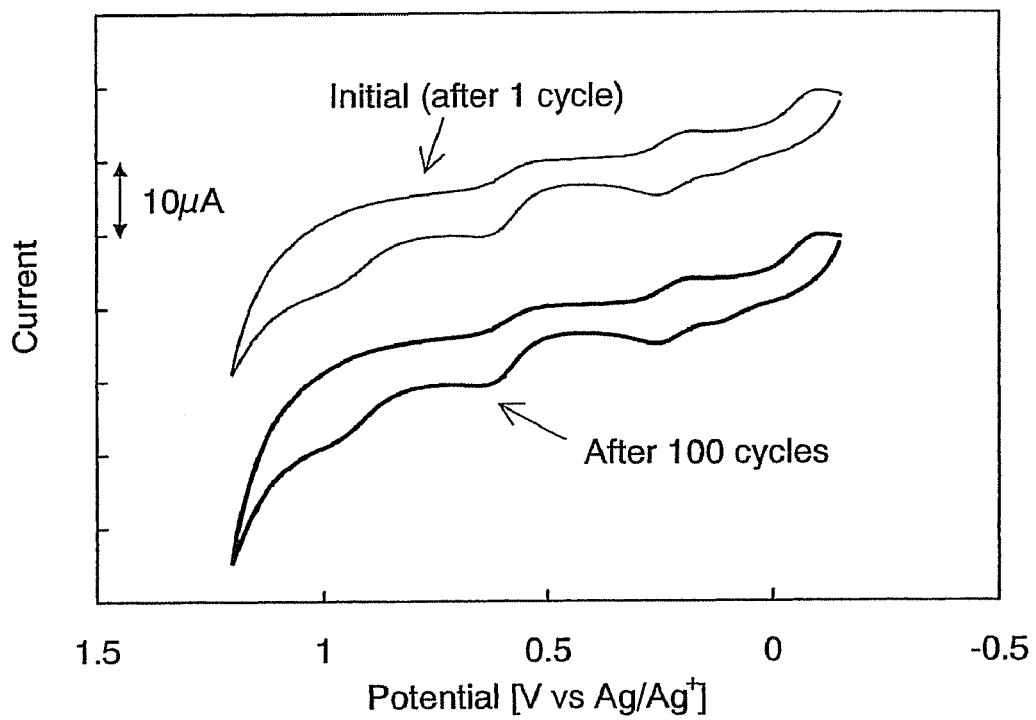
FIGS. 17A and 17B are graphs showing an oxidation reaction characteristic and a reduction reaction characteristic measured by cyclic voltammetry (CV) measurement.
Figure 17B:
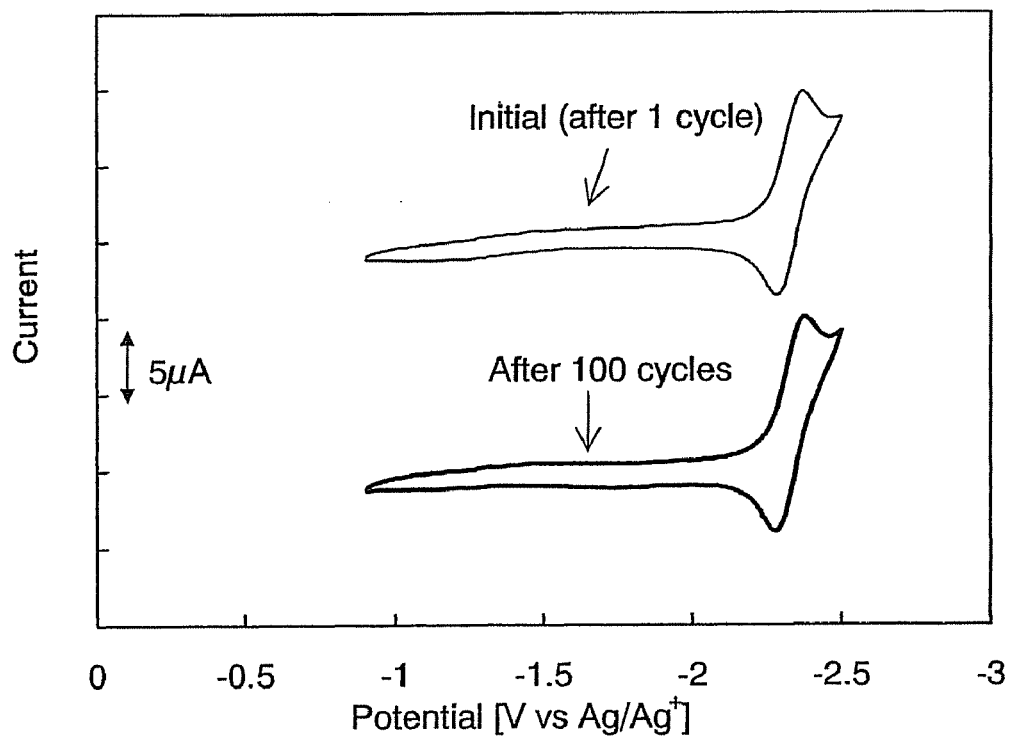

[DPABPA] Sample 4 is a quartz substrate provided with a film formed from DPABPA. The sample 4 was formed by a similar method to that of the sample 1 except for using DPABPA instead of t-BuDNA. Then, photochemical stability of the sample 4 was examined by a similar method to that of the sample 1. A change in absorption intensity of the sample 4 for a wavelength component of 400 nm with time is plotted (▲-mark) in FIG. 12. In addition, electrochemical stability of DPABPA was also examined. An oxidation reaction characteristic of DPABPA is shown in FIG. 17A and a reduction reaction characteristic of DPABPA is shown in FIG. 17B. In FIGS. 17A and 17B, each of the horizontal axes indicates an electrical potential (V) of a working electrode with respect to a reference electrode, and each of the vertical axes indicates an amount of current flowing between the working electrode and an auxiliary electrode.

Figure 18A:
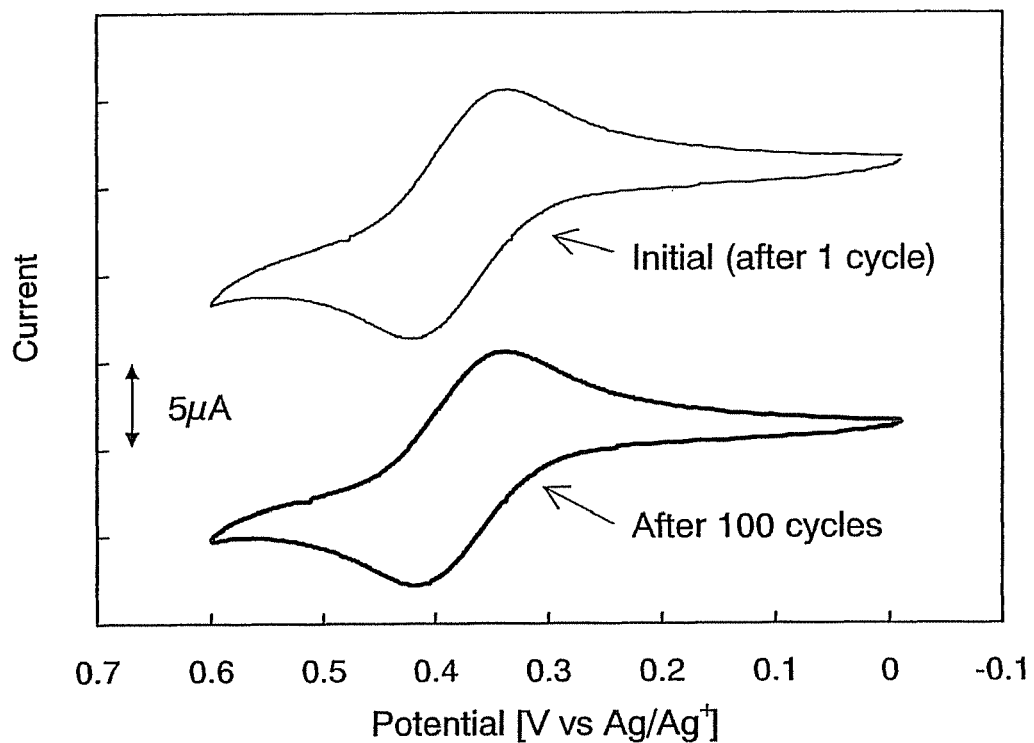
FIGS. 18A and 18B are graphs showing an oxidation reaction characteristic and a reduction reaction characteristic measured by cyclic voltammetry (CV) measurement.
Figure 18B:
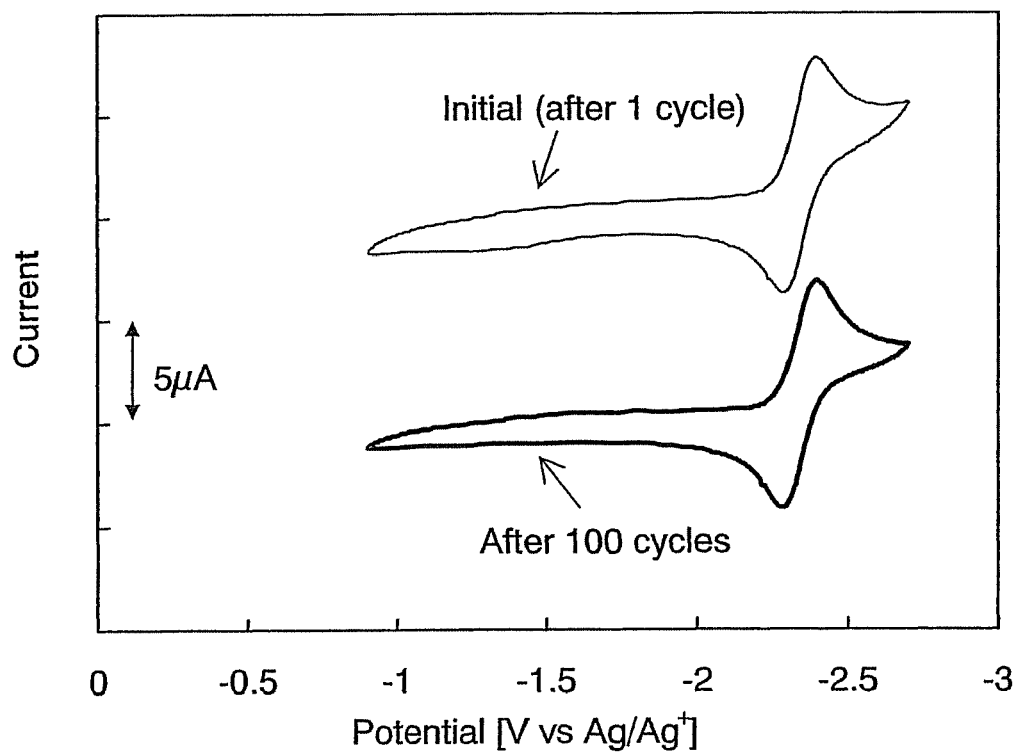

[PCABPA] Sample 5 is a quartz substrate provided with a film formed from PCABPA. The sample 5 was formed by a similar method to that of the sample 1 except for using PCABPA instead of t-BuDNA. Then, photochemical stability of the sample 5 was examined by a similar method to that of the sample 1. A change in absorption intensity of the sample 5 for a wavelength component of 400 nm with time is plotted (□-mark) in FIG. 12. In addition, electrochemical stability of PCABPA was also examined. An oxidation reaction characteristic of PCABPA is shown in FIG. 18A and a reduction reaction characteristic of PCABPA is shown in FIG. 18B. In FIGS. 18A and 18B, each of the horizontal axes indicates an electrical potential (V) of a working electrode with respect to a reference electrode, and each of the vertical axes indicates an amount of current flowing between the working electrode and an auxiliary electrode.

Figure 19A:
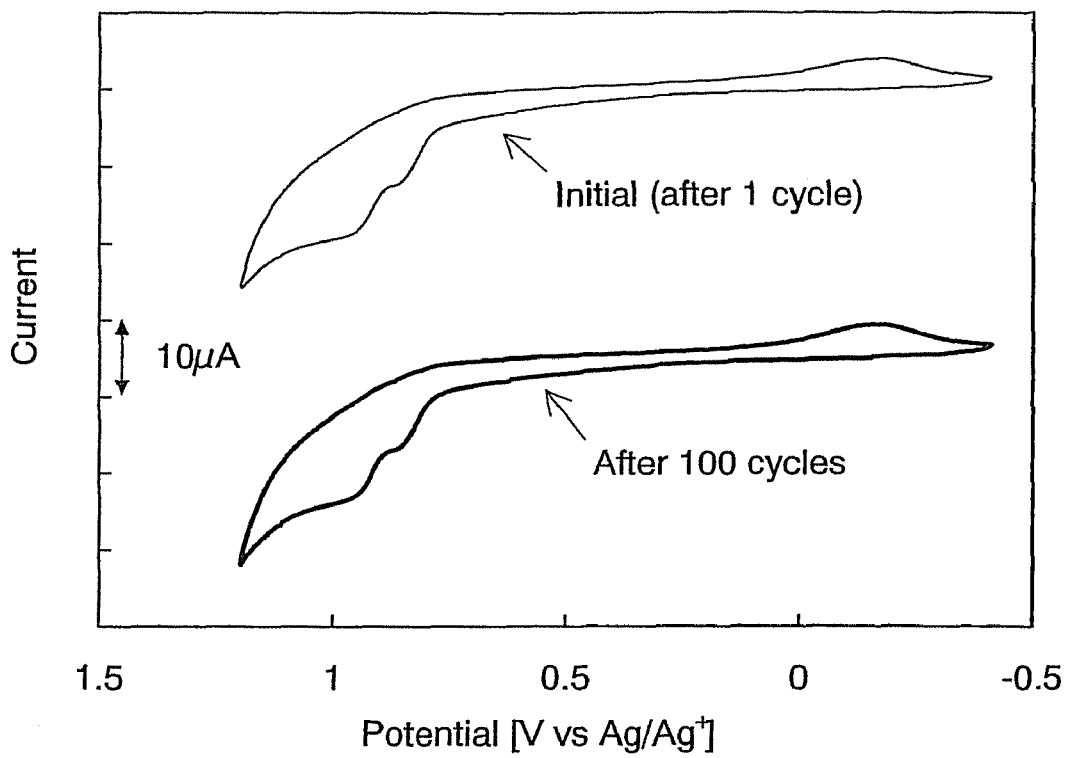
FIGS. 19A and 19B are graphs showing an oxidation reaction characteristic and a reduction reaction characteristic measured by cyclic voltammetry (CV) measurement.
Figure 19B:
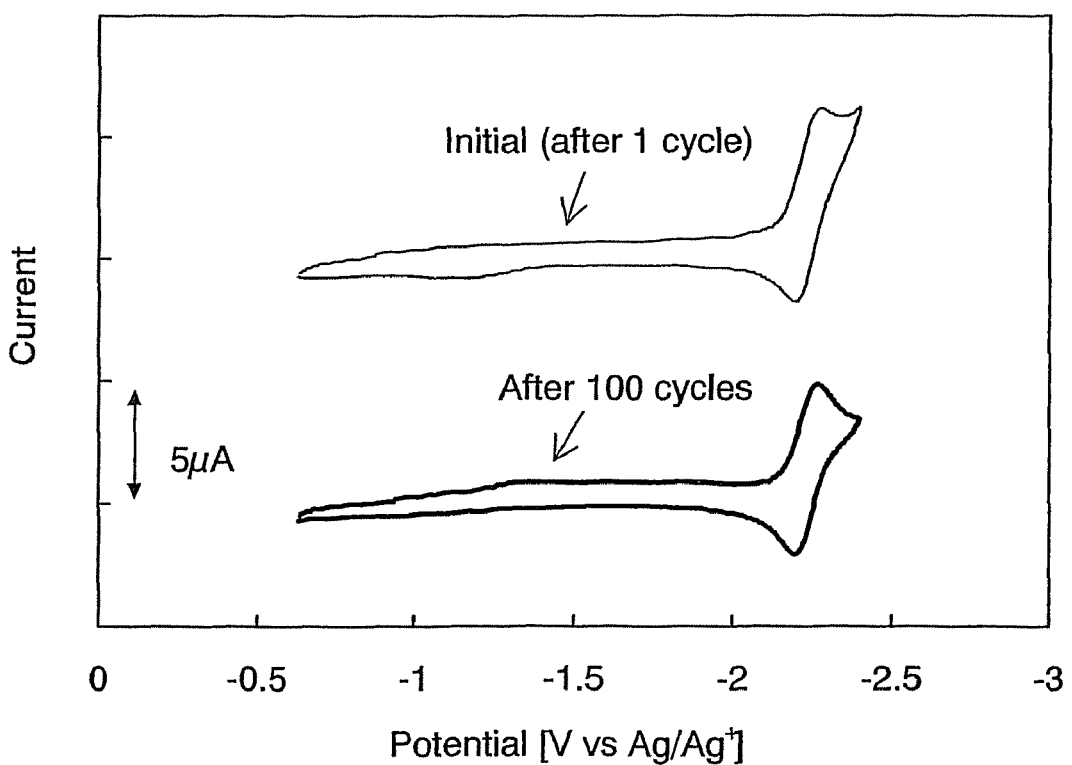

[CZPA] Sample 6 is a quartz substrate provided with a film formed from CzPA. The sample 6 was formed by a similar method to that of the sample 1 except for using CzPA instead of t-BuDNA. Then, photochemical stability of the sample 6 was examined by a similar method to that of the sample 1. A change in absorption intensity of the sample 6 for a wavelength component of 400 nm with time is plotted (*-mark) in FIG. 12. In addition, electrochemical stability of CZPA was also examined. An oxidation reaction characteristic of CZPA is shown in FIG. 19A and a reduction reaction characteristic of CzPA is shown in FIG. 19B. In FIGS. 19A and 19B, each of the horizontal axes indicates an electrical potential (V) of a working electrode with respect to the reference electrode, and each of a vertical axes indicates an amount of current flowing between the working electrode and an auxiliary electrode.

As described above, the photochemical stability and the electrochemical stability of each of the light-emitting element materials were measured. As a result, the absorption intensity of t-BuDNA decreased drastically as compared to the other materials as shown in FIG. 12, which suggests that the photochemical stability of t-BuDNA is inferior to the other light-emitting element materials used for the evaluation. In addition, as shown in each of FIGS. 13A, 13B, 15A, 15B, 16A, 16B, 17A, 17B, 18A, 18B, 19A, and 19B, although the scanning was repeated for 100 cycles, each peak position of a CV curve hardly changed in any of the light-emitting element materials. Thus, it is also known that each of the evaluated light-emitting element materials has high electrochemical stability.

Embodiment 2

In this embodiment, light-emitting elements each having CzPA or t-BuDNA as a host material is described with reference to photochemical stabilities of the elements.

A light-emitting element 1 having CzPA as a host material and a light-emitting element 2 having t-BuDNA as a host material were manufactured. The light-emitting elements 1 and 2 had the same structure except for the host materials.

First, a manufacturing method of the light-emitting elements 1 and 2 formed over a glass substrate is described. A first electrode was formed with indium tin oxide containing silicon oxide (abbreviation: ITSO) by a sputtering method over the glass substrate to have a thickness of 110 nm. The first electrode was formed to have a shape of 2 mm square. Then, a surface of the first electrode was rinsed with a porous resin (typically, a porous resin made from PVA (polyvinyl alcohol), nylon, or the like). A heat treatment at a temperature of 200° C. was carried out for one hour and UV ozone treatment was performed for 370 seconds. Then, a hole-injecting layer was formed from 4,4'-bis[N-(4-(N,N-di-m-tolylamino)phenyl)-N-phenylamino]biphenyl (hereinafter, referred to as DNTPD) over the first electrode to have a thickness of 50 nm. A hole-transporting layer was formed from NPB over the hole-injecting layer to have a thickness of 10 nm. Then, a light-emitting layer was formed of a layer containing a host material (in the case of the light-emitting element 1, CZPA was used and in the case of the light-emitting element 2, t-BuDNA was used) and DPABPA to have a thickness of 40 nm over the hole-transporting layer. Here, DPABPA was used as a guest material. The weight ratio of CzPA and DPABA was set to be CzPA:DPABPA=1:0.05. The weight ratio of t-BuDNA and DPABPA was set to be t-BuDNA:DPABPA=1:0.05. Then, an electron-transporting layer was formed from Alq over the light-emitting layer to have a thickness of 20 nm. Then, an electron-injecting layer was formed from calcium fluoride over the electron-transporting layer to have a thickness of 1 nm. Subsequently, a second electrode was formed from Al over the electron-injecting layer to have a thickness of 200 nm. Note that each of the hole-injecting layer, the hole-transporting layer, the light-emitting layer, the electron-transporting layer, the electron-injecting layer, and the second electrode was formed by a vacuum evaporation method.

Each of the light-emitting elements 1 and 2 were driven to examine a voltage at the time of starting light emission, a voltage applied in the case where light emission with a luminance of 500 cd/m$^2$ was observed, a chromaticity in the case where light emission with a luminance of 500 cd/m$^2$ was observed, and a current efficiency in the case where light emission with a luminance of 500 cd/m$^2$ was observed. The measurement result is shown in Table 1. Note that the time of starting light emission refers to a time when light emission with a luminance of 1 cd/m$^2$ or higher is observed, and a light emission start voltage refers to the voltage applied at that time.

TABLE 1

| Light-emitting element | Host | Light emission start voltage(V) | Voltage for 500 cd/m$^2$ (V) | Chromaticity (x, y) | Current efficiency of 500 cd/m$^2$(cd/A) |
|---|---|---|---|---|---|
| 1 | CzPA | 3.6 | 7.0 | (0.22, 0.43) | 9.1 |
| 2 | t-BuDNA | 3.2 | 6.6 | (0.19, 0.38) | 9.4 |

From the foregoing results described above, it is understood that each of the light-emitting elements 1 and 2 shows blue light emission efficiently.

Figure 20:
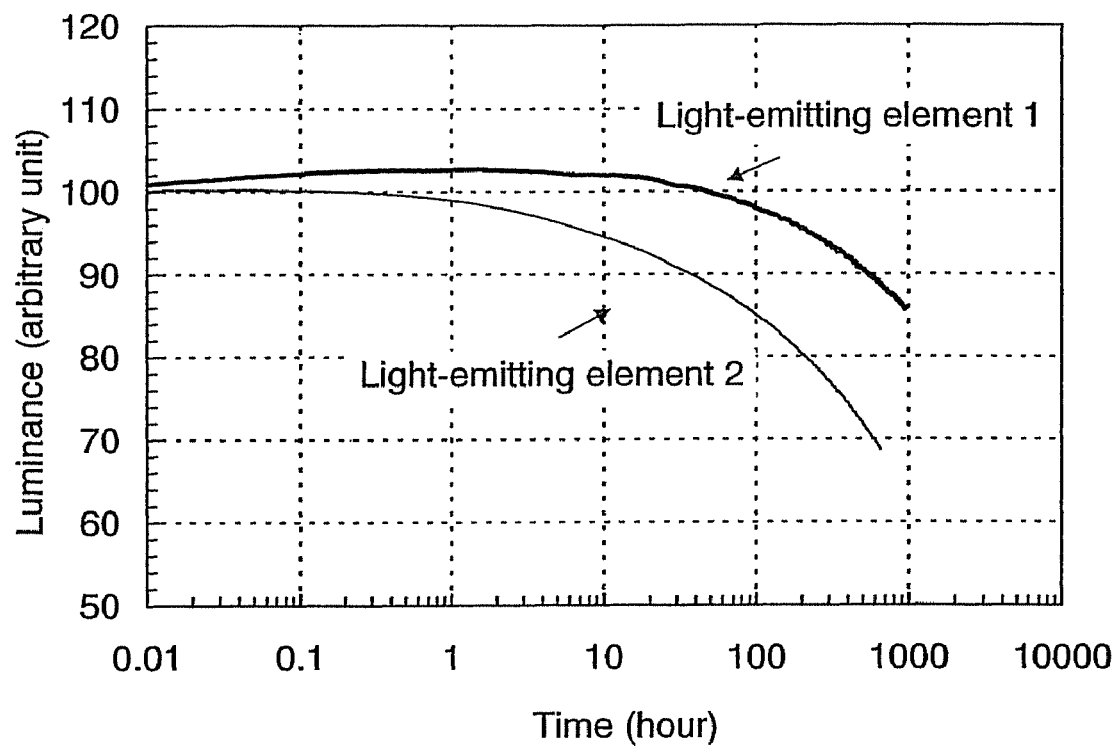
FIG. 20 is a graph showing a change in luminance associated with accumulation of light-emitting time.

Then, reliability tests of the light-emitting elements 1 and 2 were carried out. In this embodiment, reliability is assumed as a degree of deterioration in luminance (a luminance deterioration characteristic of the element) with time. The reliability test was carried out as follows. Current, which was applied to the light-emitting element when light-emission with a luminance of 500 cd/m$^2$ was obtained in an initial state, was continuously applied to the light-emitting element and luminance was measured every time a predetermined time passed. The result of the reliability test is shown in FIG. 20. In FIG. 20, the horizontal axis indicates light-emitting time (hour) and the vertical axis indicates a relative value of luminance to the initial luminance (arbitrary unit) at each of the times.

As shown in FIG. 20, it is understood that the reliability of the light-emitting element 1 is higher than that of the light-emitting element 2 since the degree of deterioration in luminance with light-emitting time of the light-emitting element 1 is smaller than that of the light-emitting element 2.

Figure 21:
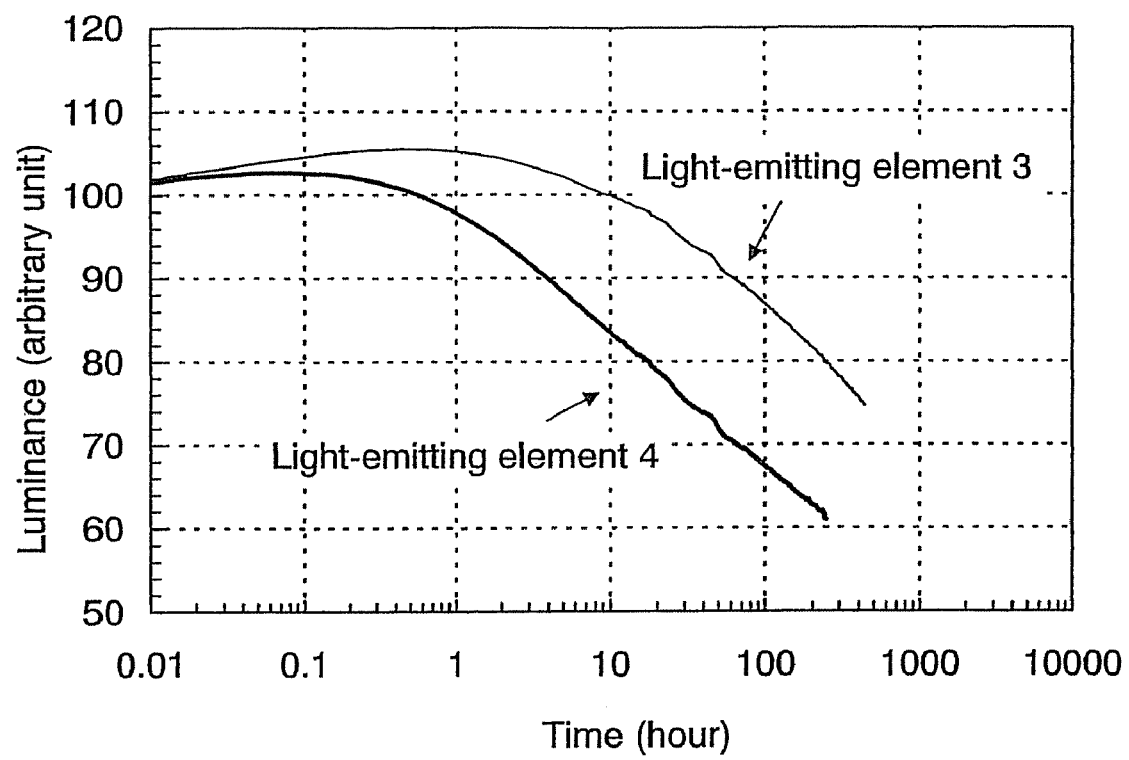
FIG. 21 is a graph showing a change in luminance associated with accumulation of light-emitting time.

Moreover, an initial characteristic and reliability of each of, a light-emitting element 3 having a similar structure to that of the light-emitting element 1 except that a guest material was PCABPA, and a light-emitting element 4 having a similar structure to that of the light-emitting element 2 except that a guest material was PCABPA, were examined. Note that the weight ratio of CZPA and PCABPA was set to be CzPA:PCABPA=1:0.05 and the weight ratio of t-BuDNA and PCABPA was set to be t-BuDNA:PCABPA=1:0.05. Current which was applied to the light-emitting element when light-emission with a luminance of 500 cd/m$^2$ was obtained in an initial state was continuously applied to the light-emitting element and luminance was measured every time a predetermined time passed, and thereby the reliability was evaluated. The examination results of the initial characteristics of the light-emitting elements 3 and 4 are shown in Table 2. The examination results of the reliability of the light-emitting elements 3 and 4 are shown in FIG. 21. As shown in FIG. 21, it is understood that the reliability of the light-emitting element 3 is higher than that of the light-emitting element 4 since the degree of deterioration in luminance with light-emitting time of the light-emitting element 3 is smaller than that of the light-emitting element 4.

TABLE 2

| Light-emitting element | Host | Voltage for starting light emission (V) | Voltage for 500 cd/m² (V) | Chromaticity (x, y) | Current efficiency of 500 cd/m²(cd/A) |
|---|---|---|---|---|---|
| 3 | CzPA | 3.0 | 4.6 | (0.17, 0.35) | 10.5 |
| 4 | t-BuDNA | 3.0 | 4.8 | (0.16, 0.32) | 11.3 |

Figure 22:
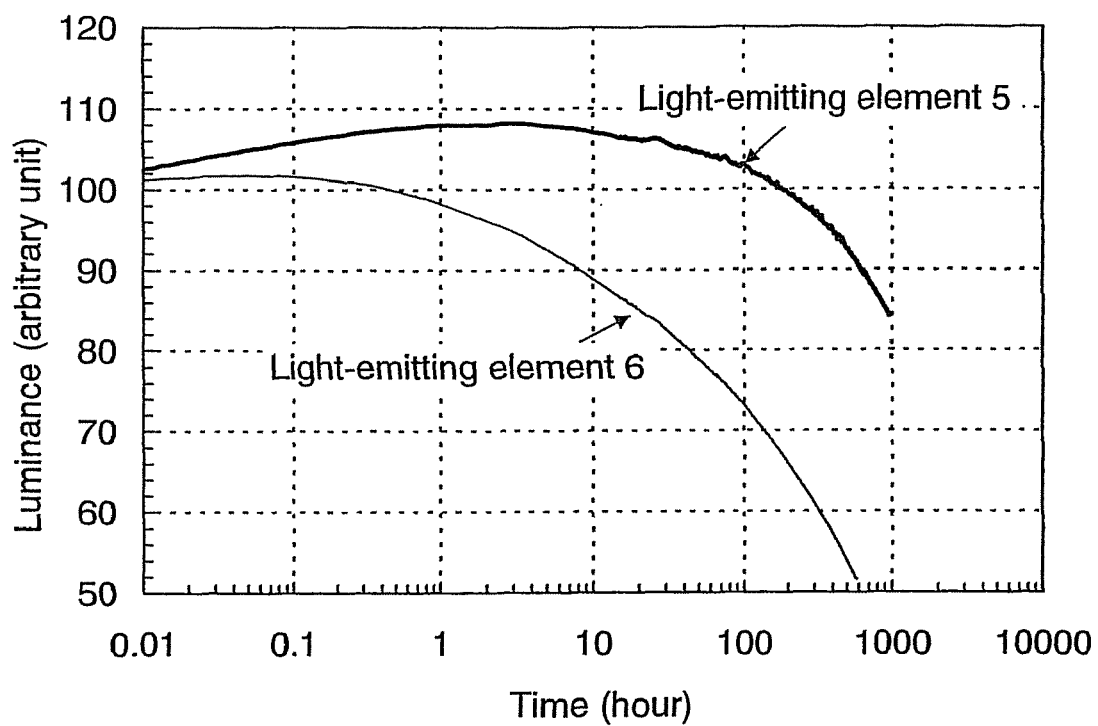
FIG. 22 is a graph showing a change in luminance associated with accumulation of light-emitting time.

Further, an initial characteristic and reliability of each of, a light-emitting element 5 having a similar structure to that of the light-emitting element 1 except that a guest material was 2,5,8,11-tetra(tert-buthyl)perylene (abbreviation: TBP) and a light-emitting element 6 having a similar structure to that of the light-emitting element 2 except that a guest material was TBP, were examined. Note that the weight ratio of CzPA and TBP was set to be CzPA:TBP=1:0.05 and the weight ratio of t-BuDNA and TBP was set to be t-BuDNA:TBP=1:0.05. Current which was applied to the light-emitting element when light-emission with a luminance of 500 cd/m² was obtained in an initial state was continuously applied to the light-emitting element and luminance was measured every time a predetermined time passed, and thereby the reliability was evaluated. The examination result of the initial characteristics of the light-emitting elements 5 and 6 are shown in Table 3. The examination results of the reliability of the light-emitting elements 5 and 6 are shown in FIG. 22. As shown in FIG. 22, it is understood that the reliability of the light-emitting element 5 is higher than that of the light-emitting element 6 since the degree of deterioration in luminance with light-emitting time of the light-emitting element 5 is smaller than that of the light-emitting element 6.

TABLE 3

| Light-emitting element | Host | Voltage for starting light emission (V) | Voltage for 500 cd/m² (V) | Chromaticity (x, y) | Current efficiency of 500 cd/m²(cd/A) |
|---|---|---|---|---|---|
| 5 | CzPA | 4.0 | 6.8 | (0.16, 0.27) | 5.0 |
| 6 | t-BuDNA | 3.4 | 6.0 | (0.15, 0.24) | 4.3 |

Figure 23:
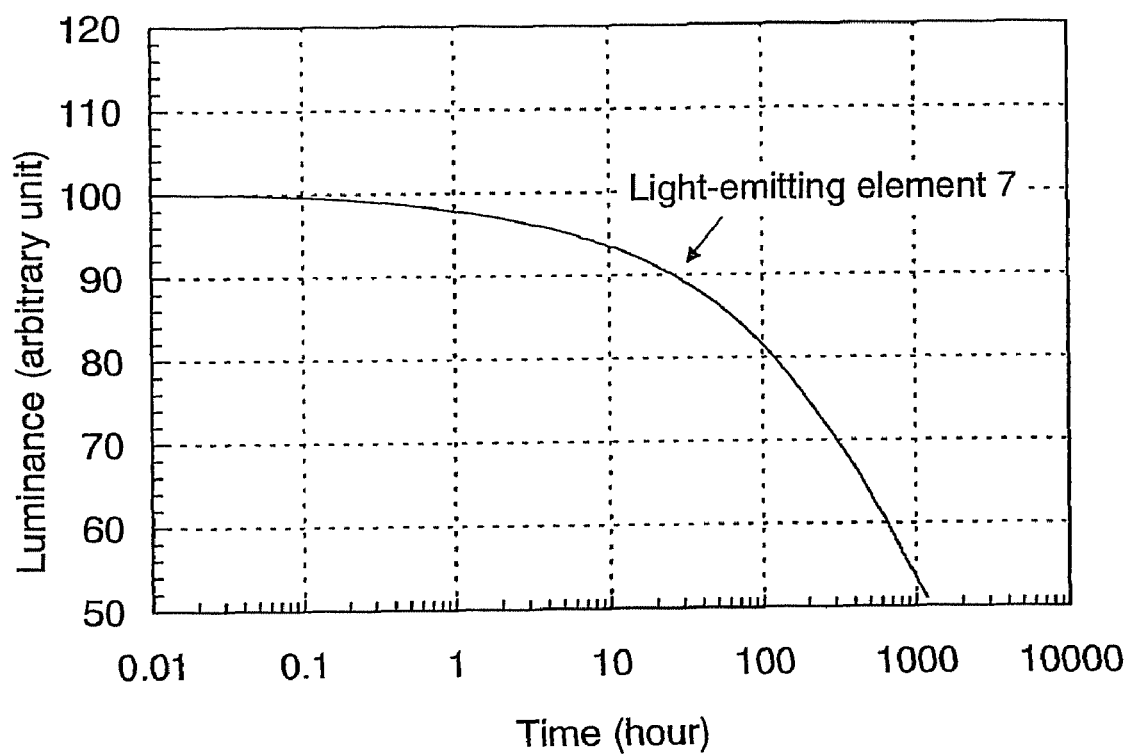
FIG. 23 is a graph showing a change in luminance associated with accumulation of light-emitting time.

Further, an initial characteristic and reliability of a light-emitting element 7 having a similar structure to that of the light-emitting element 1 except that a guest material was coumarin 6 and a host material was Alq were examined. Note that the weight ratio of Alq and coumarin 6 was set to be coumarin 6: Alq=1:0.02. Current which was applied to the light-emitting element when light-emission with a luminance of 1000 cd/m² was obtained in an initial state was continuously applied to the light-emitting element and luminance was measured every time a predetermined time passed, and thereby the reliability was evaluated. The examination result of the initial characteristic of the light-emitting element 7 is shown in Table 4. The examination result of the reliability of the light-emitting element 7 is shown in FIG. 23.

TABLE 4

| Light-emitting element | Host | Voltage for starting light emission (V) | Voltage for 1000 cd/m² (V) | Chromaticity (x, y) | Current efficiency of 1000 cd/m²(cd/A) |
|---|---|---|---|---|---|
| 7 | Alq | 2.8 | 8.8 | (0.32, 0.63) | 14.7 |

Figure 24:
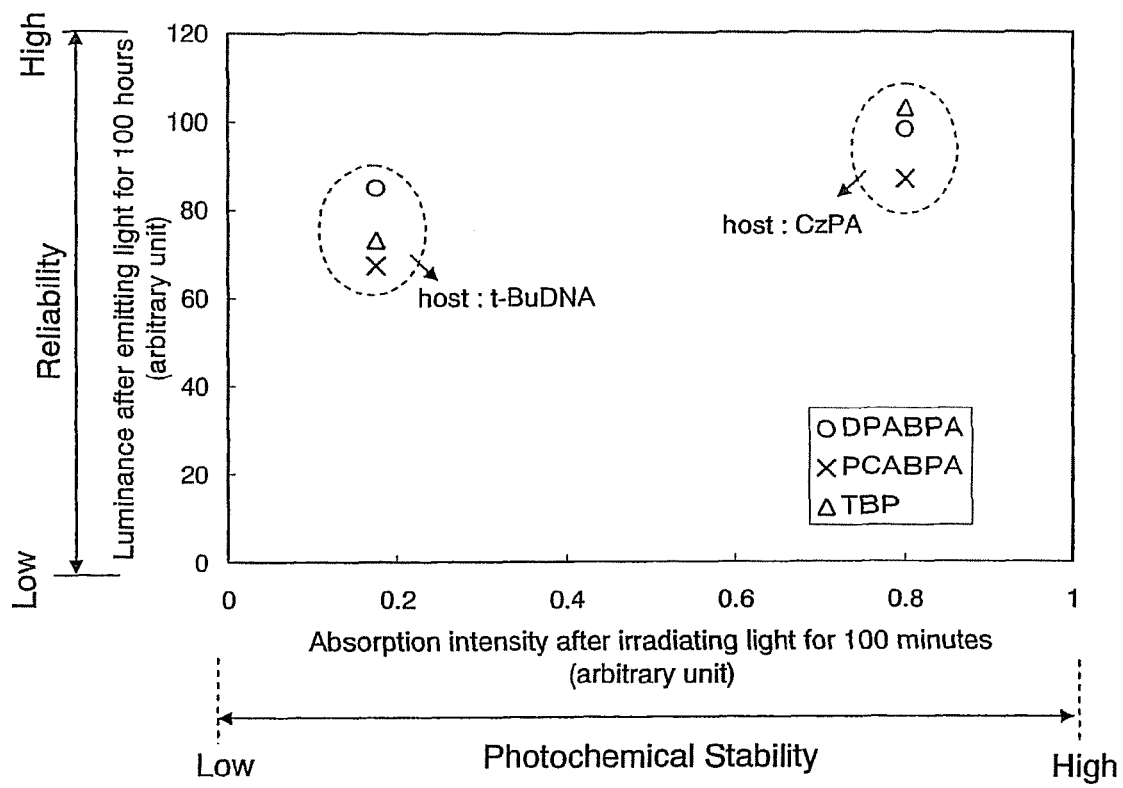
FIG. 24 is a graph for showing a correlation between photochemical stability and a deterioration characteristic of a light-emitting element associated with accumulation of light-emitting time.

Relationships between the photochemical stabilities of the host materials used for each of the light-emitting elements 1 to 6 and the reliability of each of the light-emitting elements 1 to 6 are plotted in FIG. 24. The horizontal axis indicates absorption intensity after irradiating light for 100 minutes (arbitrary unit: a relative value of the absorption intensity to that of the initial state) and the vertical axis indicates luminance after emitting light for 100 hours (arbitrary unit: a relative value of the initial luminance). Note that the absorption intensity after irradiating light for 100 minutes is obtained based on FIG. 12 and the luminance after emitting light for 100 hours is obtained based on FIGS. 20 to 23. As shown in FIG. 24, it is understood that luminance is less deteriorated with accumulation of light-emitting time in a light-emitting element using a light-emitting element material having high photochemical stability as a host material. In addition, a favorable light-emitting element with less deterioration in luminance associated with accumulation of light-emitting time can be manufactured by using an anthracene derivative such as CzPA as a host material in which a decreasing ratio of absorption intensity is 20% or less after irradiating light for 100 hours.

This application is based on Japanese Patent Application serial no. 2005-131565 Japan Patent Office on Apr. 28, 2005, the entire contents of which are hereby incorporated by reference.

What is claimed is:

1. An evaluation method of a light-emitting element material, comprising the steps of:
   measuring a first absorption intensity of the light-emitting element material;
   applying stress to the light-emitting element material after measuring the first absorption intensity;
   measuring a second absorption intensity of the light-emitting element material after applying the stress; and
   evaluating photochemical stability of the light-emitting element material based on the first absorption intensity and the second absorption intensity.

2. An evaluation method of a light-emitting element material, comprising the steps of:
   a first measuring a first absorption intensity of the light-emitting element material;
   applying stress to the light-emitting element material after the first measuring step;
   a second measuring a second absorption intensity of the light-emitting element material after applying the stress; and
   evaluating photochemical stability of the light-emitting element material based on the first absorption intensity and the second absorption intensity,
   wherein the second measuring step and the applying step are repeatedly carried out.

3. A manufacturing method of a light-emitting device including a light-emitting layer containing a light-emitting element material between a first electrode and a second electrode, comprising the steps of:
   measuring a first absorption intensity of the light-emitting element material;
   applying stress to the light-emitting element material after measuring the first absorption intensity;
   measuring a second absorption intensity of the light-emitting element material after applying the stress;
   evaluating photochemical stability of the light-emitting element material based on the first absorption intensity and the second absorption intensity; and
   forming the light-emitting layer containing the light-emitting element material after the evaluating step.

4. An evaluation method of a light-emitting element material according to claim 1, wherein the light-emitting element material is an anthracene derivative.

5. An evaluation method of a light-emitting element material according to claim 2, wherein the light-emitting element material is an anthracene derivative.

6. A manufacturing method of a light-emitting device according to claim 3, wherein the light-emitting element material is an anthracene derivative.

7. An evaluation method of a light-emitting element material according to claim 1, wherein the stress is light.

8. An evaluation method of a light-emitting element material according to claim 2, wherein the stress is light.

9. A manufacturing method of a light-emitting device according to claim 3, wherein the stress is light.

10. An evaluation method of a light-emitting element material according to claim 1, wherein the light-emitting element material is evaluated by difference between the first absorption intensity and the second absorption intensity.

11. An evaluation method of a light-emitting element material according to claim 2, wherein the light-emitting element material is evaluated by difference between the first absorption intensity and the second absorption intensity.

12. A manufacturing method of a light-emitting device according to claim 3, wherein the light-emitting element material is evaluated by difference between the first absorption intensity and the second absorption intensity.

13. A manufacturing method of a light-emitting device according to claim 3, wherein the light-emitting device is incorporated into an electric appliance selected from the group consisting of a laptop personal computer, a portable phone, a television receiver, a car navigation system, a camera, and a lighting apparatus.

14. A manufacturing method of a light-emitting device according to claim 3, wherein the first electrode and the second electrode are formed by a material selected from the group consisting of indium tin oxide, indium tin oxide containing silicon oxide, indium oxide containing 2 to 20% of zinc oxide, gold, platinum, nickel, tungsten, chromium, molybdenum, iron, cobalt, copper, palladium, aluminum, an alloy of magnesium and silver, and an alloy of aluminum and lithium.

* * * * *